(12) United States Patent
Deng et al.

(10) Patent No.: US 12,205,717 B2
(45) Date of Patent: Jan. 21, 2025

(54) SYSTEMS AND METHODS FOR DETERMINING BLOOD PRESSURE OF SUBJECT

(71) Applicant: VITA-COURSE DIGITAL TECHNOLOGIES (TSINGTAO) CO., LTD., Shangdong (CN)

(72) Inventors: Ziming Deng, Shenzhen (CN); Chuanmin Wei, Shenzhen (CN); Ying Lu, Shenzhen (CN); Zijian Huang, Shenzhen (CN); Jiwei Zhao, Shenzhen (CN); Kezheng Ma, Shenzhen (CN); Mengcheng Hu, Shenzhen (CN)

(73) Assignee: VITA-COURSE DIGITAL TECHNOLOGIES (TSINGTAO) CO., LTD., Tsingtao (CN)

( * ) Notice: Subject to any disclaimer, the term of this patent is extended or adjusted under 35 U.S.C. 154(b) by 956 days.

(21) Appl. No.: 17/044,398

(22) PCT Filed: Apr. 13, 2018

(86) PCT No.: PCT/CN2018/082902
§ 371 (c)(1),
(2) Date: Oct. 1, 2020

(87) PCT Pub. No.: WO2019/196076
PCT Pub. Date: Oct. 17, 2019

(65) Prior Publication Data
US 2021/0100455 A1 Apr. 8, 2021

(51) Int. Cl.
*G16H 40/67* (2018.01)
*A61B 5/00* (2006.01)
(Continued)

(52) U.S. Cl.
CPC .............. *G16H 40/67* (2018.01); *A61B 5/021* (2013.01); *A61B 5/7275* (2013.01);
(Continued)

(58) Field of Classification Search
CPC ........ G16H 50/70; G16H 40/67; G06F 18/23; G06F 18/213; G06F 18/2131;
(Continued)

(56) References Cited

U.S. PATENT DOCUMENTS

2004/0122485 A1* 6/2004 Stahmann .............. G16H 10/20
607/60
2015/0164375 A1 6/2015 Schindhelm et al.
(Continued)

FOREIGN PATENT DOCUMENTS

CA 2840795 A1 1/2013
CA 2840795 C * 10/2018 ............... A61B 5/01
(Continued)

OTHER PUBLICATIONS

Z. Yongfang, C. Xiaohui and Z. Yongsheng, "Non-invasive Real-time Blood Pressure Prediction Method Based on Machine Learning," 2018 5th IEEE International Conference on Cloud Computing and Intelligence Systems (CCIS), Nanjing, China, 2018, pp. 588-592, doi: 10.1109/CCIS.2018.8691328. (Year: 2018).*
(Continued)

*Primary Examiner* — Yi-Shan Yang
*Assistant Examiner* — Jonathan E. Cooper
(74) *Attorney, Agent, or Firm* — Metis IP LLC

(57) ABSTRACT

A method implemented on a computing device having at least one processor, storage, and a communication platform connected to a network for determining blood pressure includes: receiving a request to determine a blood pressure of a first subject from a terminal, obtaining data relating to the first subject, the data relating to the first subject including
(Continued)

data relating to heart activity of the first subject and personal information relating to the first subject, extracting target features relating to the first subject from the data relating to the first subject, determining a preliminary blood pressure of the first subject using a prediction model based on the target features relating to the first subject, determining a predicted blood pressure of the first subject using an optimization model based on the preliminary blood pressure and sending the predicted blood pressure of the first subject to the terminal in response to the request.

20 Claims, 13 Drawing Sheets

(51) Int. Cl.
    *A61B 5/021*     (2006.01)
    *G06F 18/2131*     (2023.01)
    *G06F 18/23*     (2023.01)
    *G16H 50/70*     (2018.01)

(52) U.S. Cl.
    CPC .......... *G06F 18/2131* (2023.01); *G06F 18/23* (2023.01); *G16H 50/70* (2018.01)

(58) Field of Classification Search
    CPC ..... A61B 5/021; A61B 5/7275; A61B 5/0022; A61B 5/0205
    USPC ........................................................ 600/485
    See application file for complete search history.

(56) References Cited

U.S. PATENT DOCUMENTS

| | | | | |
|---|---|---|---|---|
| 2016/0278644 | A1* | 9/2016 | He | A61B 5/7275 |
| 2017/0042433 | A1 | 2/2017 | Noh et al. | |
| 2017/0071485 | A1 | 3/2017 | Huang et al. | |
| 2017/0132816 | A1* | 5/2017 | Aston | A61B 5/346 |
| 2017/0258340 | A1* | 9/2017 | Przybyszewski | A61B 5/7267 |
| 2018/0116597 | A1 | 5/2018 | Yu et al. | |
| 2018/0116600 | A1* | 5/2018 | Basu | A61B 5/0245 |
| 2018/0132744 | A1 | 5/2018 | Yu et al. | |
| 2018/0151254 | A1* | 5/2018 | Han | G06F 18/24133 |
| 2018/0214068 | A1* | 8/2018 | Munne | C12Q 1/6883 |
| 2019/0046122 | A1* | 2/2019 | Schnetz | A61B 5/7264 |
| 2020/0320335 | A1* | 10/2020 | Shamun | G06N 3/08 |
| 2021/0121083 | A1* | 4/2021 | Edo | A61B 5/7275 |
| 2022/0079459 | A1 | 3/2022 | Lu et al. | |

FOREIGN PATENT DOCUMENTS

| | | | | | |
|---|---|---|---|---|---|
| CN | 101288586 | A | | 10/2008 | |
| CN | 1985750 | B | | 3/2011 | |
| CN | 102429649 | A | | 5/2012 | |
| CN | 102397064 | B | | 2/2014 | |
| CN | 106343976 | A | | 1/2017 | |
| CN | 106691406 | A | | 5/2017 | |
| CN | 106777891 | A | * | 5/2017 | .............. G06F 19/32 |
| CN | 106889979 | A | | 6/2017 | |
| CN | 106923807 | A | | 7/2017 | |
| CN | 107847153 | A | | 3/2018 | |
| CN | 107847156 | A | | 3/2018 | |
| CN | 106659404 | B | | 2/2020 | |
| JP | 2014000105 | A | | 1/2014 | |
| JP | 2016016295 | A | | 2/2016 | |
| WO | 2017167013 | A1 | | 10/2017 | |
| WO | 2018052635 | A1 | | 3/2018 | |

OTHER PUBLICATIONS

International Search Report in PCT/CN2018/082902 mailed on Jan. 2, 2019, 5 pages.

Written Opinion in PCT/CN2018/082902 mailed on Jan. 2, 2019, 4 pages.

* cited by examiner

SYSTEMS AND METHODS FOR DETERMINING BLOOD PRESSURE OF SUBJECT

CROSS-REFERENCE TO RELATED APPLICATIONS

This application is a U.S. national stage under 35 U.S.C. § 371 of International Application No. PCT/CN2018/082902, filed on Apr. 13, 2018, the content of which is hereby incorporated by reference in its entirety.

TECHNICAL FIELD

The present disclosure generally relates to systems and methods applicable in health-care related areas. More particularly, the present disclosure relates to systems and methods for determining a blood pressure of a subject.

BACKGROUND

Blood pressure measurement can be categorized into invasive blood pressure measurement and non-invasive blood pressure measurement. Invasive blood pressure measurement is usually used in medical surgeries or medical research and needs to be conducted by the medical professionals. Non-invasive blood pressure measuring is an indirect blood pressure measuring method. A sphygmomanometer is a popular non-invasive blood pressure measuring device. It is composed of an inflatable cuff to collapse and then release the artery under the cuff in a controlled manner, and a mercury or mechanical manometer to measure the pressure. However, frequent measuring using the sphygmomanometer causes discomfort of the subject as frequent inflation oppresses the blood vessels of the subject. Further, the accuracy of the measured blood pressure is affected by the size of the cuff, elastic effects and the posture of the subject during the measurement.

Another non-invasive blood pressure measurement system may collect many physiological characteristics data of a plurality of subjects (e.g. patients or a person) as sample data to build a model for predicting a blood pressure of the subject. As the physiological characteristics data of a plurality of subjects is in huge amount, the dimensions of the characteristics are high, and includes outlier sample data, it is difficult to build the model to predict a blood pressure of the subject. Therefore, there is a need to provide an accurate, efficient and personalized blood pressure prediction model by reducing the high dimensions of the characteristics yet without deleting the outlier sample data.

SUMMARY

According to one aspect of the present disclosure, a system for determining a blood pressure is provided. The system may include at least one storage medium including a set of instructions, a communication platform connected to a network; and at least one processor in communication with the at least one storage medium. When executing the set of instructions, the at least one processor may be directed to receive a request to determine a blood pressure of a first subject from a terminal. The at least one processor may obtain data relating to the first subject, wherein the data relating to the first subject may include data relating to heart activity of the first subject and personal information relating to the first subject. The at least one processor may extract target features relating to the first subject from the data relating to the first subject. The at least one processor may determine a preliminary blood pressure of the first subject using a prediction model based on the target features relating to the first subject. The at least one processor may determine a predicted blood pressure of the first subject using an optimization model based on the preliminary blood pressure. The at least one processor may also send the predicted blood pressure of the first subject to the terminal in response to the request.

According to another aspect of the present disclosure, a method implemented on a computing device having at least one processor, storage, and a communication platform connected to a network for determining a blood pressure is provided. The method may include receiving a request to determine a blood pressure of a first subject from a terminal. The method may include obtaining data relating to the first subject, wherein the data relating to the first subject may include data relating to heart activity of the first subject and personal information relating to the first subject. The method may include extracting target features relating to the first subject from the data relating to the first subject. The method may include determining a preliminary blood pressure of the first subject using a prediction model based on the target features relating to the first subject. The method may include determining a predicted blood pressure of the first subject using an optimization model based on the preliminary blood pressure. The method may also include sending the predicted blood pressure of the first subject to the terminal in response to the request.

According to another aspect of the present disclosure, a non-transitory computer-readable medium including at least one set of instructions for determine blood pressure is provided. When executed by at least one processor, the at least one set of instructions may direct the at least one processor to receive a request to determine a blood pressure of a first subject from a terminal. The at least one processor may also obtain data relating to the first subject, wherein the data relating to the first subject may include data relating to heart activity of the first subject and personal information relating to the first subject. The at least one set of instructions may direct the at least one processor to extract target features relating to the first subject from the data relating to the first subject. The at least one set of instructions may direct the at least one processor to determine a preliminary blood pressure of the first subject using a prediction model based on the target features relating to the first subject. The at least one set of instructions may direct the at least one processor to determine a predicted blood pressure of the first subject using an optimization model based on the preliminary blood pressure. The at least one set of instructions may also direct the at least one processor to send the predicted blood pressure of the first subject to the terminal in response to the request.

In some embodiments, to obtain the data relating to the heart activity of the first subject, the at least one processor may be further directed to communicate with a device connected to the first subject, the device being configured to detect the heart activity of the first subject and generate a signal and receive from the device, the data relating to heart activity of the first subject generated based on the signal.

In some embodiments, the prediction model may be generated via a first training process. The first training process may include obtaining historical data relating to a plurality of second subjects and a plurality of historical blood pressure measurements associated with the plurality of second subjects, wherein the plurality of second subjects may include the first subject, and the historical data relating to the plurality of second subjects may include data relating to heart activities of the plurality of second subjects and historical personal information relating to the plurality of second subjects. The first training process may also include generating a preliminary prediction model based on the historical data relating to the plurality of second subjects and the plurality of historical blood pressure measurements associated with the plurality of second subjects; and generating the prediction model with respect to the first subject based on the preliminary prediction model and at least part of the historical data relating to the first subject.

In some embodiments, the generating the preliminary prediction model based on the historical data relating to the plurality of second subjects and the plurality of historical blood pressure measurements associated with the plurality of second subjects may include extracting a first set of features from the historical data relating to the plurality of second subjects; determining a second set of features based on the first set of features, a dimension of the second set of features being less than a dimension of the first set of features; clustering the historical data relating to the plurality of second subjects into one or more clusters; determining historical target features based on the second set of features; for each cluster of the one or more clusters, determining a sub prediction model based on the historical target features of the historical data in the each cluster and the historical blood pressure measurements corresponding to the historical data in the each cluster; and designating the one or more sub prediction modes corresponding to the one or more clusters as the preliminary prediction model.

In some embodiments, the generating the preliminary prediction model based on the historical data relating to the plurality of second subjects and the plurality of historical blood pressure measurements associated with the plurality of second subjects may further include normalizing the historical data relating to the plurality of second subjects before extracting the first set of features from the historical data relating the plurality of second subjects.

In some embodiments, the second set of features may be determined using a principal component analysis technique.

In some embodiments, the generating the prediction model with respect to the first subject based on the preliminary prediction model and the at least part of the historical data relating to the first subject may include extracting historical target features from the historical data relating to the first subject; determining a target cluster from the one or more clusters based on the historical target features of the historical data relating to the first subject; and designating the sub prediction mode corresponding the target cluster as the prediction model with respect to the first subject.

In some embodiments, to determine the predicted blood pressure of the first subject using the optimization model based on the preliminary blood pressure, the at least one processor may be further directed to: initialize a first optimization model; designate the preliminary blood pressure as a first blood pressure; iteratively perform: generating a second blood pressure based on the first blood pressure using the first optimization model; determining whether a converging condition is satisfied based on the first blood pressure and the second blood pressure; in response to a determination that the converging condition is satisfied, designating the first optimization model as the optimization model and designating the second blood pressure generated in the iteration as the predicted blood pressure; and in response to a determination that the converging condition is not satisfied, updating the first optimization model and designating the second blood pressure generated in the iteration as the first blood pressure.

In some embodiments, to initialize the first optimization model, the at least one processor may be directed to: obtain a historical blood pressure measurement of the first subject and historical target features of the first subject; and initialize the first optimization model based on the historical blood pressure measurement of the first subject and the historical target features of the first subject.

In some embodiments, the predicted blood pressure of the first subject may include a systolic blood pressure and a diastolic blood pressure. The systolic blood pressure may be predicted based on the diastolic blood pressure using the optimization model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
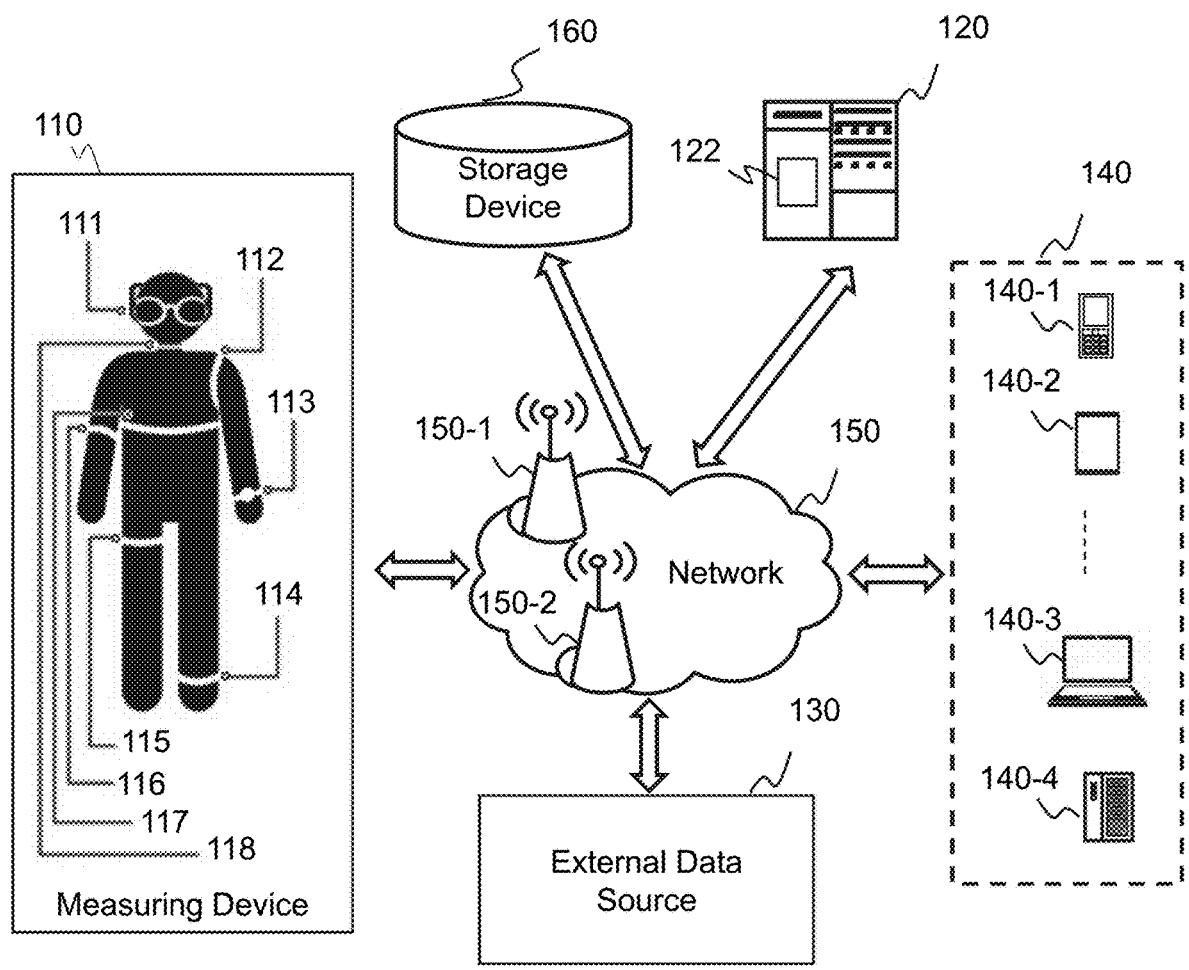
FIG. 1 illustrates an exemplary system configuration in which a medical system may be deployed in accordance with some embodiments of the present disclosure.

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

An aspect of the present disclosure relates to systems and methods for determining a blood pressure of a first subject (also referred to herein as a target subject). The present disclosure predicts a preliminary blood pressure of the first subject using a prediction model based on data relating to the first subject. The prediction model is trained using a sample data set of blood pressure measurements associated with a large amount of subjects. The data relating to the first subject may include data relating to the heart activities of the first subject and the personal information relating to the first subject. The present disclosure further employs an optimization model to generate a predicted blood pressure of the first subject based on the preliminary blood pressure. The optimization model utilizes the correlation between the systolic blood pressure and the diastolic blood pressure of a subject to determine the systolic blood pressure and the diastolic blood pressure during each iteration to achieve more accurate blood pressure prediction result.

FIG. 1 illustrates an exemplary system configuration in which a medical system 100 may be deployed in accordance with some embodiments of the present disclosure. The medical system 100 may be configured to monitor a physiological parameter of interest. The medical system 100 may include a measuring device 110, a server 120, an external data source 130, a terminal 140, and a storage device 160. Various components of the medical system 100 may be connected to each other directly or indirectly via a network 150.

The measuring device 110 may be configured to detect physiological phenomenon (e.g., heart activities) of a subject and generate a signal. The signal may be a cardiovascular signal. The signal may relate to or be used to determine a physiological parameter of interest. The measuring device 110 may include, for example, a clinical device, a household device, a portable device, a wearable device, or the like, or a combination thereof. As used herein, a clinical device may be one that meets applicable requirements and specifications to be used in a clinical setting including, e.g., a hospital, a doctor's office, a nursing home, or the like. A clinical device may be used by or with the assistance of a medical worker. As used herein, a household device may be one that meets applicable requirements and specifications to be used at home or a nonclinical setting. A household device may be used by someone who is or is not a professional provider. A clinical device or a household device, or a portion thereof, may be portable or wearable. Exemplary clinical devices include an auscultatory device, an oscillometric device, an ECG monitor, a PPG monitor, or the like, or a combination thereof. Exemplary household devices include an oscillometric device, a household ECG monitor, a sphygmometer, or the like, or a combination thereof. Exemplary portal devices include an oscillometric device, a portable ECG monitor, a portable PPG monitor, or the like, or a combination thereof. Exemplary wearable devices include a pair of glasses 111, a shoulder strap 112, a smart watch 113, an anklet 114, a thigh band 115, an armband 116, a chest belt 117, a necklet 118, or the like, or a combination thereof. The above-mentioned examples of measuring devices 110 are provided for illustrative purposes, and not intended to limit the scope of the present disclosure. A measuring device 110 may be in other forms, such as a fingerstall, a wristband, a brassiere, an underwear, a chest band, a pulse oximeter, or a device associated with the principle used in a pulse oximeter, or the like, or a combination thereof.

Merely by way of example, the measuring device 110 is a wearable or portable device configured to detect and generate one or more cardiovascular signals. In some embodiments, the wearable or portable device may process at least some of the measured signals, estimate a physiological parameter of interest based on the measured signals, display a result including the physiological parameter of interest in the form of, e.g., an image, an audio alert, perform wired or wireless communication with another device or server (e.g., the server 120), or the like, or a combination thereof. In some embodiments, the wearable or portable device may communicate with another device (e.g., the terminal 140) or a server (e.g., the server 120). The device or server may process at least some of the measured signals, estimate a physiological parameter of interest based on the measured signals, display a result including the physiological parameter of interest in the form of, e.g., an image, an audio alert, or the like, or a combination thereof.

In some embodiments, the operations of processing the generated signals, estimating a physiological parameter, displaying a result, or performing wired or wireless communication may be performed by an integrated device or by separate devices connected to or communicating with each other. Such an integrated device may be portable or wearable. In some embodiments, at least some of the separate devices may be portable or wearable, or located in the vicinity of a subject from which the signal is measured or a physiological parameter of interest is estimated or monitored. Merely by way of example, the subject wears the measuring device 110 that is configured to detect and generate one or more cardiovascular signals; and the generated one or more cardiovascular signals are transmitted to a smart phone that is configured to determine a physiological parameter of interest based on the measured signals. In some embodiments, at least some of the separate devices are located in a location remote from the subject. Merely by way of example, the subject wears the measuring device 110 that is configured to detect and generate one or more cardiovascular signals; the generated one or more cardiovascular signals are further transmitted to the server 120 that is configured to determine a physiological parameter of interest based on the measured signals; and the determined physiological parameter of interest may be transmitted back to the subject, or a user other than the subject (e.g., a doctor, a care provider, a family member relating to the subject, or the like, or a combination thereof).

In some embodiments, the measuring devices 110 may incorporate various types of sensors, e.g., an electrode sensor, an optical sensor, a photoelectric sensor, a pressure sensor, an accelerometer, a gravity sensor, a temperature sensor, a moisture sensor, or the like, or a combination thereof. The measuring device 110 may be configured to monitor and/or detect one or more types of variables including, for example, temperature, humidity, user or subject input, or the like, or a combination thereof. The gravity sensor may detect the posture of the measured subject. The posture may include lying, sitting, standing, etc. The temperature sensor may detect the temperature of a position near the measuring device 110. The moisture sensor may detect the humidity of an area near the measuring device 110. The measuring device 110 may also incorporate a positioning system, e.g., a GPS receiver, or a location sensor, and the position information may be transmitted to the server 120, the external data source 130, the terminal 140, or the like, or a combination thereof, through the network 150. The position information and measured signals may be transmitted simultaneously or successively. In some embodiments, the measuring device 110 may incorporate one or more computer chips on which the functions of the server 120 as described below may be implemented.

The server 120 may be a cloud server. Merely by way of example, the server 120 may be implemented in a cloud server that may provide storage capacity, computation capacity, or the like, or a combination thereof. The server 120 may include a storage device configured to collect or store data. The data may include personal data, non-personal data, or both. The data may include static data, dynamic data, or both. Exemplary static data may include various information regarding a subject including identity, contact information, birthday, a health history (e.g., whether a subject has a history of smoking, information regarding a prior surgery, a food allergy, a drug allergy, a medical treatment history, a history of genetic disease, a family health history, or the like, or a combination thereof), the gender, the nationality, the height, the weight, the occupation, a habit (e.g., a health-related habit such as an exercise habit), the education background, a hobby, the marital status, religious belief, or the like, or a combination thereof. Exemplary dynamic data may include a current health condition of a subject, medications the subject is taking, a medical treatment the subject is undertaking, diet, physiological signals or parameters (e.g., pulse transit time (PTT), systolic blood pressure (SBP), diastolic blood pressure (DBP), or the like) relating to the subject for multiple time points or over a period of time, or the like, or a combination thereof.

As used herein, a subject may refer to a person or animal whose signal or information is acquired and whose physiological parameter is determined or monitored. Merely by way of example, a subject may be a patient whose cardiovascular signals are acquired, and blood pressure determined or monitored based on the acquired cardiovascular signals.

In some embodiments, the server 120 may be a single server, or a server group. The server group may be centralized, or distributed (e.g., server 110 may be a distributed system). In some embodiments, the server 120 may be local or remote. For example, the server 120 may access information and/or data stored in the terminal 140 and/or the storage device 160 via the network 150. As another example, the server 120 may connect the terminal 140 and/or the storage device 160 to access stored information and/or data. In some embodiments, the server 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the server 120 may be implemented on a computing device 200 having one or more components illustrated in FIG. 2 in the present disclosure.

In some embodiments, the server 120 may include a processing engine 122. The processing engine 122 may process information and/or data to perform one or more functions described in the present disclosure. For example, the processing engine 122 may determine blood pressure of a subject based on one or more personalized models, data related to the generated signals, and/or information related to the subject. In some embodiments, the processing engine 122 may include one or more processing engines (e.g., single-core processing engine(s) or multi-core processor(s)). Merely by way of example, the processing engine 122 may include one or more hardware processors, such as a central processing unit (CPU), an application-specific integrated circuit (ASIC), an application-specific instruction-set processor (ASIP), a graphics processing unit (GPU), a physics processing unit (PPU), a digital signal processor (DSP), a field programmable gate array (FPGA), a programmable logic device (PLD), a controller, a microcontroller unit, a reduced instruction-set computer (RISC), a microprocessor, or the like, or any combination thereof.

The external data source 130 may include a variety of organizations, systems, and devices, or the like, or a combination thereof. Exemplary data source 130 may include a medical institution, a research facility, a conventional device, and a peripheral device, or the like, or a combination thereof. The medical institution or the research facility may provide, for example, personal medical records, clinical test results, experimental research results, theoretical or mathematical research results, algorithms suitable for processing data, or the like, or a combination thereof. The conventional device may include a cardiovascular signal measuring device, such as a mercury sphygmomanometer. A peripheral device may monitor and/or detect one or more types of variables including, for example, temperature, humidity, user or subject input, or the like, or a combination thereof. The above-mentioned examples of the external data sources 130 and data types are provided for illustration purposes, and not intended to limit the scope of the present disclosure. For instance, the external data source 130 may include other sources and other types of data, such as genetic information relating to a subject or his family.

The terminal 140 in the medical system 100 may be configured for processing at least some of the generated signals, determining a physiological parameter of interest based on the generated cardiovascular signals, displaying a result including the physiological parameter of interest in the form of, e.g., an image, storing data, controlling access to the medical system 100 or a portion thereof (e.g., access to the personal data stored in the medical system 100 or accessible from the medical system 100), managing input-output from or relating to a subject, or the like, or a combination thereof.

The terminal 140 may include a mobile device 140-1, a tablet computer 140-2, a laptop computer 140-3, a built-in device in a motor vehicle 140-4, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, a smart footgear, a smart glass, a smart helmet, a smart watch, a smart clothing, a smart backpack, a smart accessory, or the like, or any combination thereof. In some embodiments, the smart mobile device may include a smartphone, a personal digital assistance (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass™, a RiftCon™, a Fragments™, a Gear VR™, etc. In some embodiments, built-in device in the motor vehicle 140-4 may include an onboard computer, an onboard television, etc.

The network 150 may facilitate exchange of information and/or data. In some embodiments, one or more components of the medical system 100 (e.g., the measuring device 110, the server 120, the external data source 130, the terminal 140, and the storage device 160) may transmit information and/or data to other component(s) in the medical system 100 via the network 150. For example, the server 120 may receive a request for determining blood pressure of a subject from the terminal 140 via the network 150. In some embodiments, the network 150 may be any type of wired or wireless network, or combination thereof. Merely by way of example, the network 150 may include a cable network, a wireline network, an optical fiber network, a tele communications network, an intranet, an Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In some embodiments, the network 150 may include one or more network access points. For example, the network 150 may include wired or wireless network access points such as base stations and/or internet exchange points 150-1, 150-2, . . . , through which one or more components of the medical system 100 may be connected to the network 150 to exchange data and/or information between them.

The storage device 160 may store data and/or instructions. In some embodiments, the storage device 160 may store data obtained from the terminal 140. In some embodiments, the storage device 160 may store data and/or instructions that the server 120 may execute or use to perform exemplary methods described in the present disclosure. In some embodiments, the storage device 160 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 160 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 160 may be connected to the network 150 to communicate with one or more components of the medical system 100 (e.g., the measuring device 110, the server 120, the external data source 130, the terminal 140, and the storage device 160). One or more components in the medical system 100 may access the data or instructions stored in the storage device 160 via the network 150. In some embodiments, the storage device 160 may be directly connected to or communicate with one or more components in the medical system 100 (e.g., the measuring device 110, the server 120, the external data source 130, the terminal 140, and the storage device 160).

In some embodiments, one or more components of the service medical system 100 (e.g., the measuring device 110, the server 120, the external data source 130, the terminal 140, and the storage device 160) may access the storage device 160. For example, the server 120 may read and/or modify one or more users' information after a request for predicting blood pressure of a subject.

In some embodiments, various components of the medical system 100 may include a storage device for storing intermediate data and/or information. Such components may include, for example, the measuring device 110, the server 120, the external data source 130, the terminal 140, or the like, or a combination thereof.

In some embodiments, the external data source 130 may receive data from the measuring device 110, the server 120, the terminal 140, or the like, or any combination via the network 150. Merely by way of example, the external data source 130 (e.g., a medical institution, or a smart home system, or the like) may receive information related to a subject (e.g., location information, data from the cloud server or a terminal, or the like, or a combination thereof) based on the data received from the measuring device 110 or the terminal 140. In some other embodiments, the measuring device 110 may receive data from the server 120, the external data source 130, or the like, or any combination, via the network 150. Merely by way of example, the measuring device 110 may receive the information related to a subject (e.g., a current/historical health condition of a subject, medications the subject is taking, medical treatment the subject is undertaking, current/historical diets, current emotion status, historical physiological parameters (e.g., PTT, SBP, DBP) relating to the subject, or the like, or a combination thereof). Furthermore, the terminal 140 may receive data from the measuring device 110, the server 120, the external data source 130, or the like, or a combination thereof. In some embodiments, the server 120 may store one or more personalized models for predicting blood pressure and may transmit the personalized models to the measuring device 110 and the terminal 140.

It should be noted that the description about the configuration of the medical system 100 is not intended to limit the scope of the present disclosure. In some embodiments, the server 120 may be omitted, migrating all of its functions to the terminal 140. In some embodiments, the server 120 and the terminal 140 may both be omitted, migrating all of their functions to the measuring device 110. The system may include various devices or combinations of devices in different embodiments.

Figure 2:
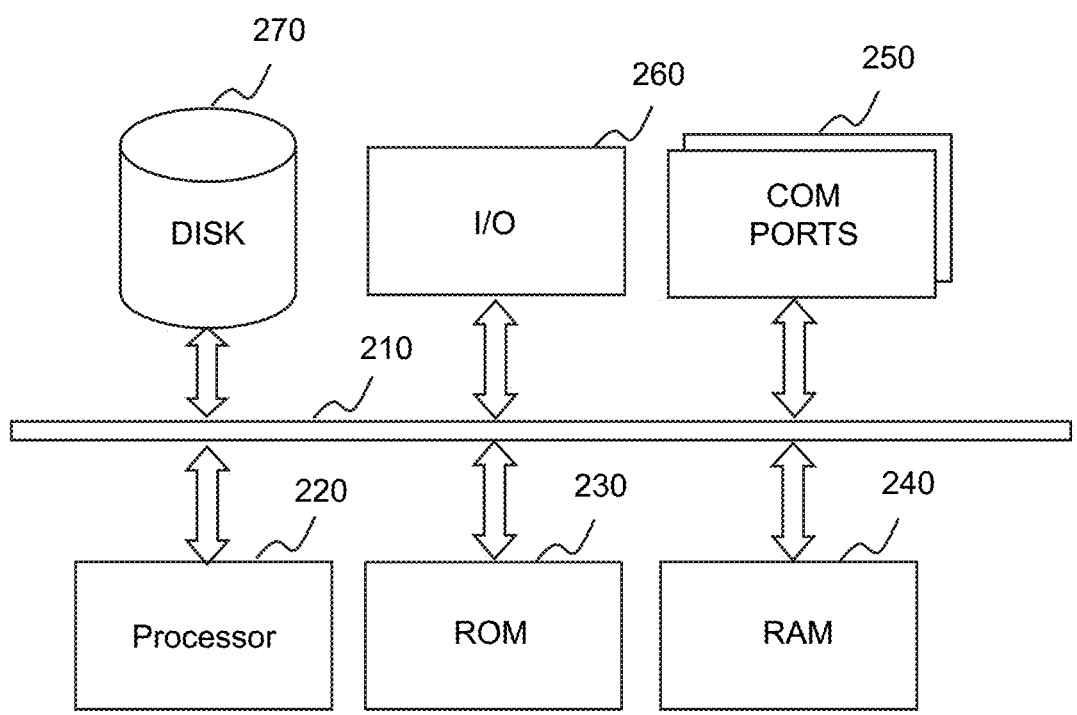
FIG. 2 is a schematic diagram illustrating exemplary hardware and software components of a computing device according to some embodiments of the present disclosure.

FIG. 2 is a schematic diagram illustrating exemplary hardware and software components of a computing device 200 which may be implemented on the measuring device 110, the server 120, the external data source 130, the terminal 140, and the storage device 160 according to some embodiments of the present disclosure. For example, the processing engine 122 may be implemented on the computing device 200 and configured to perform functions of the processing engine 122 disclosed in this disclosure.

The computing device 200 may be a general-purpose computer or a special purpose computer; both may be used to implement a system for the present disclosure. The computing device 200 may be used to implement any component of the as described herein. For example, the processing engine 122 may be implemented on the computing device 200, via its hardware, software program, firmware, or a combination thereof. Although only one such computer is shown, for convenience, the computer functions relating to the medical system 100 as described herein may be implemented in a distributed fashion on a number of similar platforms, to distribute the processing load.

The computing device 200, for example, may include COM ports 250 connected to and from a network connected thereto to facilitate data communications. The computing device 200 may also include a processor (e.g., the processor 220), in the form of one or more processors, for executing program instructions. The exemplary computing device may include an internal communication bus 210, program storage and data storage of different forms including, for example, a disk 270, and a read only memory (ROM) 230, or a random access memory (RAM) 240, for various data files to be processed and/or transmitted by the computing device. The exemplary computing device may also include program instructions stored in the ROM 230, RAM 240, and/or other type of non-transitory storage medium to be executed by the processor 220. The methods and/or processes of the present disclosure may be implemented as the program instructions. The computing device 200 also includes an I/O component 260, supporting input/output between the computer and other components. The computing device 200 may also receive programming and data via network communications.

Merely for illustration, only one CPU and/or processor is illustrated in FIG. 2. Multiple CPUs and/or processors are also contemplated; thus, operations and/or method steps performed by one CPU and/or processor as described in the present disclosure may also be jointly or separately performed by the multiple CPUs and/or processors. For example, if in the present disclosure the CPU and/or processor of the computing device 200 executes both step A and step B, it should be understood that step A and step B may also be performed by two different CPUs and/or processors jointly or separately in the computing device 200 (e.g., the first processor executes step A and the second processor executes step B, or the first and second processors jointly execute steps A and B).

Figure 3:
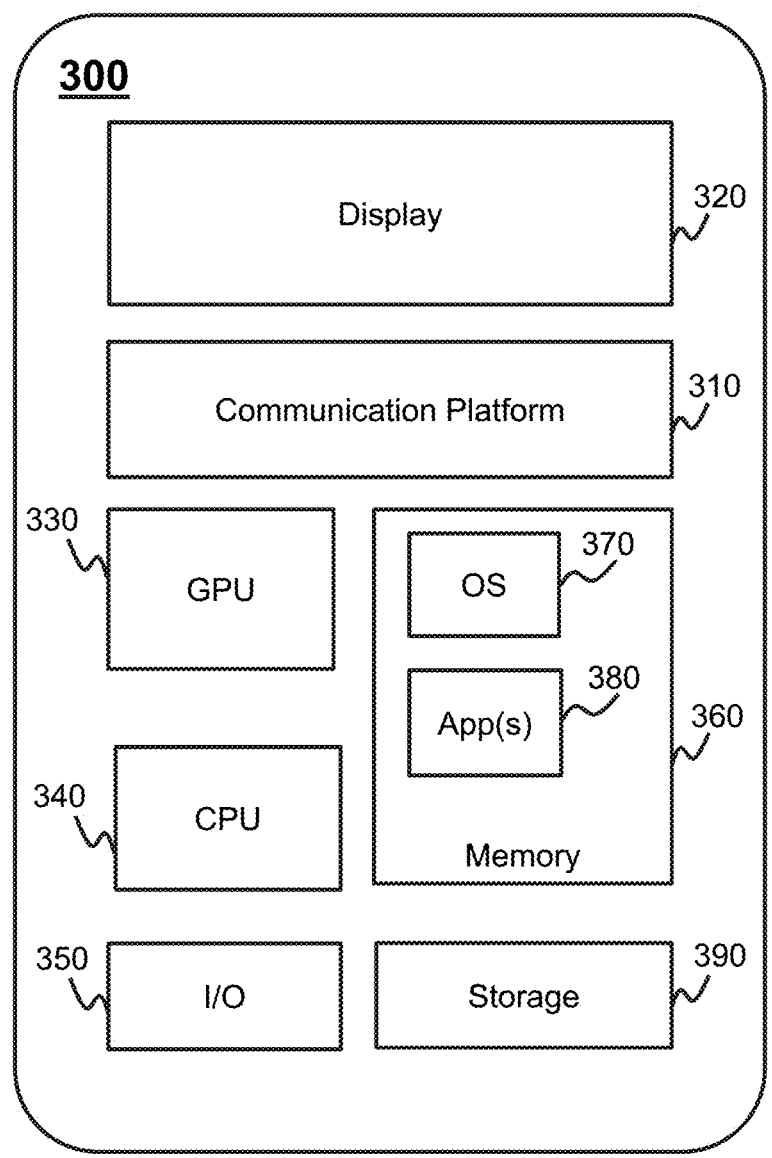
FIG. 3 is a schematic diagram illustrating exemplary hardware and/or software components of an exemplary mobile device on which a use terminal may be implemented according to some embodiments of the present disclosure.

FIG. 3 is a schematic diagram illustrating exemplary hardware and/or software components of an exemplary mobile device 300 on which a use terminal may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 122. User interactions with the information stream may be achieved via the I/O 350 and provided to the processing engine 122 and/or other components of the medical system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
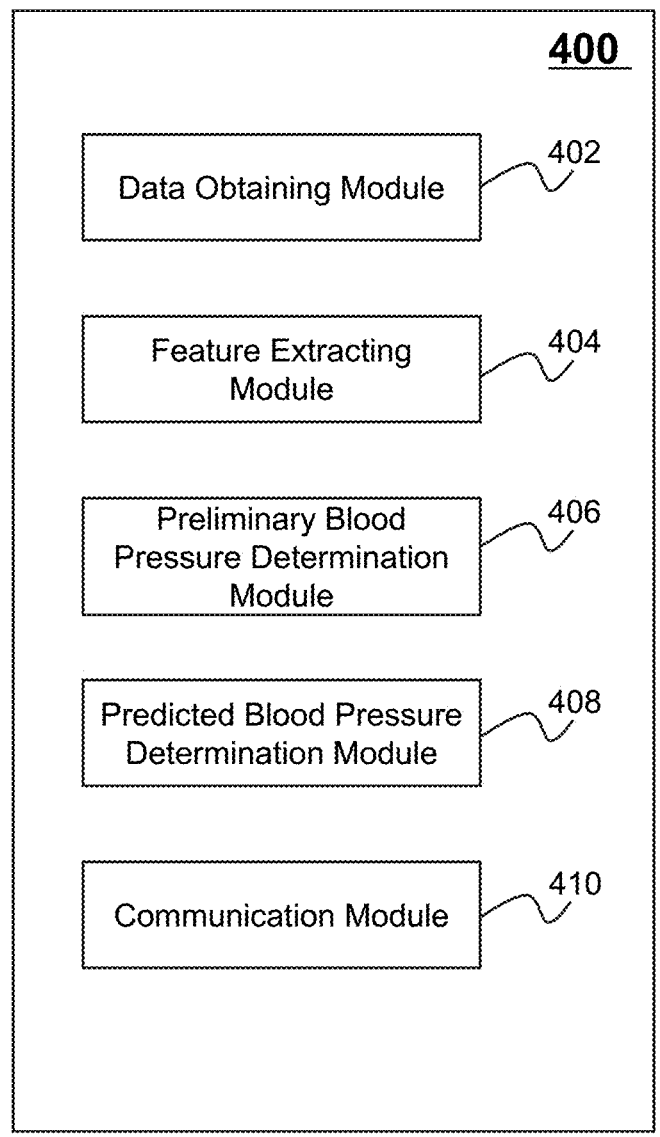
FIG. 4 is a block diagram illustrating an exemplary processor according to some embodiments of the present disclosure.

FIG. 4 is a block diagram illustrating an exemplary processor according to some embodiments of the present disclosure. The processor 400 may include a data obtaining module 402, a feature extracting module 404, a preliminary blood pressure determination module 406, a predicted blood pressure determination module 408, and a communication module 410. Each module may be a hardware circuit that is designed to perform the following actions, a set of instructions stored in one or more storage media, and/or any combination of the hardware circuit and the one or more storage media. The modules in the processor 400 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. In some embodiments, any two of the modules may be combined as a single module, and any one of the modules may be divided into two or more units.

The data obtaining module 402 may obtain data relating to the first subject. The data relating to the first subject may include data relating to the heart activities of the first subject and the personal information relating to the first subject. Merely by way of example, the signal may be physiological signals including but not limited to an electrocardiogram (ECG) signal, a pulse-wave-related signal (e.g., photoplethysmogram (PPG)), a phonocardiogram (PCG) signal, an impedance cardiogram (ICG) signal, or the like, or any combination thereof. The personal information relating to the first subject may include the gender of the first subject, age of the subject, height of the first subject, weight of the first subject, posture of the first subject at a time when the signal is obtained, the time when the signal is obtained, whether or not the first subject is with high blood pressure, whether or not the first subject is under at least one medication, information relating to the at least one medication, names and birthdays of family members, addresses and phone numbers of family members' homes, emergency contact information, list of current medications and doses, list of allergies, list of any medical devices (e.g., pacemakers), list of current doctors and office phone numbers, insurance card copies, DNR (do not resuscitate) orders and form, Power of Attorney (POA) forms, or the like, or a combination thereof. The posture of the first subject at the time when the signal is obtained may include lying, sitting, standing, etc.

The feature extracting module 404 may extract target features relating to the first subject from the data relating to the first subject obtained by the data obtaining module 402. The target features may refer to the features relating to the prediction of the blood pressure of the first subject.

The preliminary blood pressure determination module 406 may determine a preliminary blood pressure of the first subject. In some embodiments, the preliminary blood pressure determination module 406 may determine the preliminary blood pressure of the first subject using the prediction model based on the target features relating to the first subject. The target features may be used as inputs of the prediction model. Then the preliminary blood pressure determination module 406 may designate the output of the prediction model as the preliminary blood pressure of the first subject. The preliminary blood pressure may include a systolic blood pressure and a diastolic blood pressure. In some embodiments, the prediction model may be trained in advance.

The predicted blood pressure determination module 408 may determine the predicted blood pressure of the first subject using the optimization model based on the preliminary blood pressure of the first subject to optimize the preliminary blood pressure. In some embodiments, the optimization model may be trained in advance, and the optimization model may be stored in the server 120 (e.g., a cloud server), the terminal 140, and/or the storage device 160. The predicted blood pressure determination module 408 may obtain the optimization model from the server 120, the terminal 140, and/or the storage device 160 correspondingly. In some embodiments, the optimization model may be determined by performing one or more operations described in connection with FIG. 13.

The communication module 410 may receive a request to determine a blood pressure of a first subject from the terminal 140. The communication module 410 may also send the predicted blood pressure of the first subject to the terminal 140 in response to the request. The terminal 140 may correspond to the first subject. For example, the first subject may be the user of the terminal 140.

In some embodiments, all of the modules in FIG. 4 may be implemented by a single processor of one component of the medical system 100, e.g., the measuring device 110, the server 120, or the terminal 140. In some embodiments, one or more modules in FIG. 4 may be implemented by different processors in one component of the medical system 100, e.g., the measuring device 110, the server 120, or the terminal 140. In some embodiments, one or more modules described in FIG. 4 may be implemented by different processors in different components of the medical system 100, e.g., the measuring device 110, the server 120, or the terminal 140. For example, the modules 402, 406, 408, and 410 may be implemented by a processor in the server 120. As another example, modules 402 and 410 may be implemented by a first processor in the terminal 140, and modules 404, 406, and 408 may be implemented by a second processor in the terminal 140. As still another example, modules 402 and 410 may be implemented by a first processor in the server 120, and modules 404, 406, and 408 may be implemented by a second processor in the server 120. As yet another example, modules 402 and 410 may be implemented by a processor in the measuring device 110, and modules 404, 406, and 408 may be implemented by a processor in the server 120. As still another example, module 402 may be implemented by a processor in the measuring device 110, modules 404, 406, and 408 may be included in a processor in the server 120, and module 410 may be implemented by a processor in the terminal 140.

Figure 5:
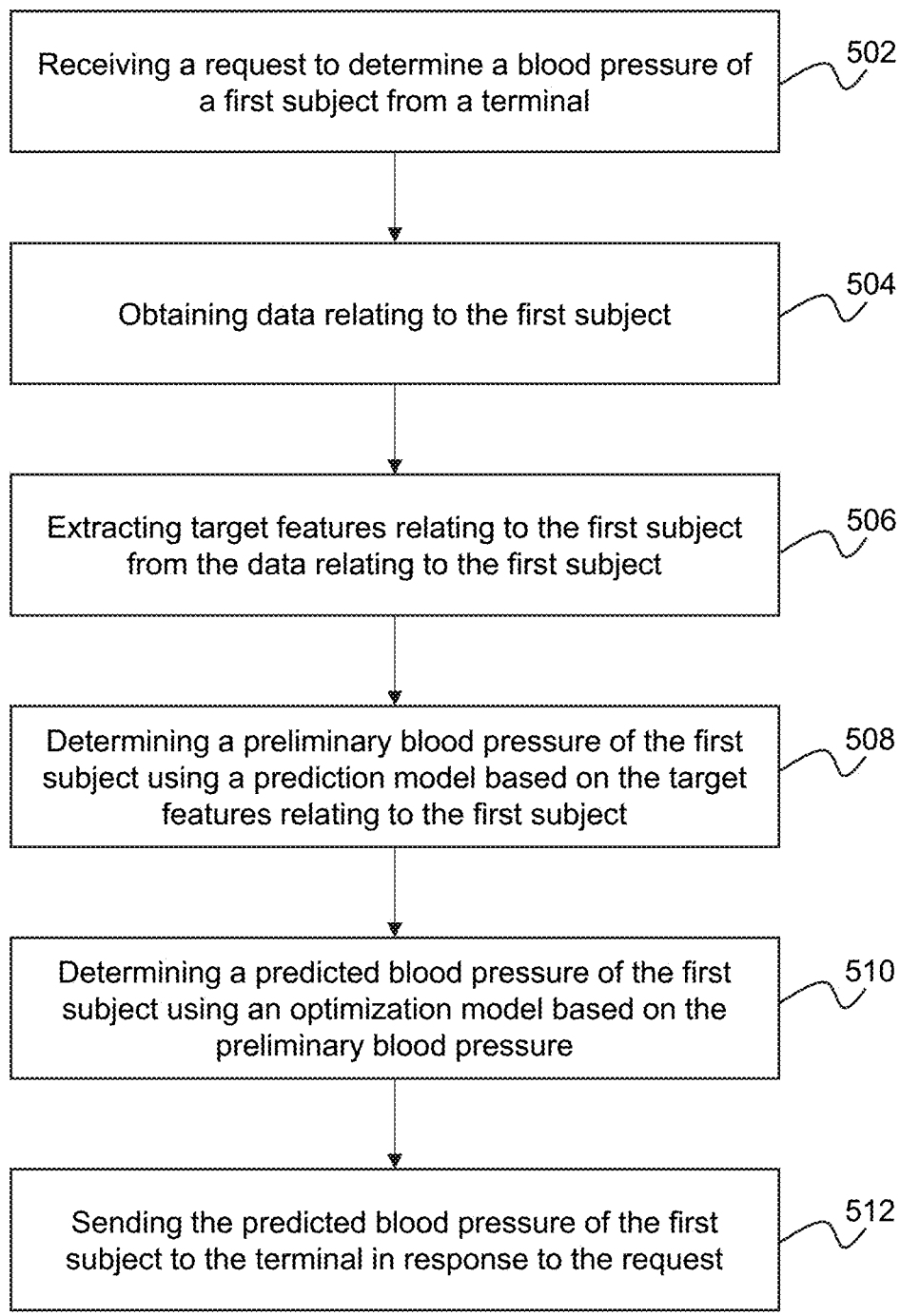
FIG. 5 is a flow chart illustrating a process and/or method for providing a blood pressure of a first subject to a terminal in response to a request according to some embodiments of the present disclosure.

FIG. 5 is a flow chart illustrating a process and/or method 500 for providing a blood pressure of a first subject to a terminal in response to a request according to some embodiments of the present disclosure. The process and/or method 500 may be executed by the medical system 100 (e.g., the terminal 140, the server 120). For example, the process and/or method 500 may be implemented as a set of instructions (e.g., an application) stored in the storage ROM 230 or RAM 240. The processor 220 (e.g., the processor 400) may execute the set of instructions and may accordingly be directed to perform the process and/or method 500. The operations of the illustrated process/method presented below are intended to be illustrative. In some embodiments, the process/method may be accomplished with one or more additional operations not described, and/or without one or more of the operations discussed. Additionally, the order in which the operations of the process/method as illustrated in FIG. 5 and described below is not intended to be limiting. It should also be noted that the process and/or method 500 may be implemented in the measuring device 110, the server 120, the terminal 140, and/or any combination thereof.

In 502, the processor 400 (e.g., the communication module 410) may receive a request to determine a blood pressure of a first subject from the terminal 140. In some embodiments, the user may initiate and send the request by the terminal. In some embodiments, a person other than the user (e.g., a medical worker) may initiate and send the request by the terminal.

In 504, the processor 400 (e.g., the data obtaining module 402) may obtain data relating to the first subject.

In some embodiments, the data relating to the first subject may include data relating to the heart activities of the first subject. The data relating to the heart activities of the first subject may include data related to a signal indicative of the heart activities of the first subject. Merely by way of example, the signal may be physiological signals including but not limited to an electrocardiogram (ECG) signal, a pulse-wave-related signal (e.g., photoplethysmogram (PPG)), a phonocardiogram (PCG) signal, an impedance cardiogram (ICG) signal, or the like, or any combination thereof.

The measuring device 110 may be attached to the first subject and detect the heart activities of the first subject. The measuring device 110 may generate the signal indicative of the heart activities by the detecting. The processor 400 (e.g., the data obtaining module 402) may receive the data relating to the heart activities of the first subject generated based on the signal from the measuring device 110 through the communication module 410.

The signal may be stable for a predetermined time period. The predetermined time period may be default settings of the medical system 100 or adjusted in different conditions. The predetermined time period may be any time span (e.g., 10 seconds, 15 seconds, 20 seconds, 30 seconds, etc.). A wave form representing the signal may be displayed on a user interface of a terminal (e.g., the terminal 140). The signal within the predetermined time period may include a plurality of beats of the heart of the first subject.

For each beat of the signal, the wave may include one or more characteristic points (e.g., wave crest, trough of the wave, etc.). The data relating to the heart activities of the first subject may include first data relating to the signal, e.g., a time value, an amplitude value, an area value, a derivative related to each of the one or more the characteristic points, etc. The time value and the amplitude value of a characteristic point may be the abscissa and the ordinate of the characteristic point, respectively. The area value may be an integral relating to a time interval. The area value may indicate the change of the blood volume in a vessel close to the attached measuring device 110. The derivative may include a first derivative, a second derivative, a third derivative, a higher derivative, or the like, or a combination thereof. For the plurality of beats, the processor 400 may determine a plurality of time values, a plurality of amplitude values, a plurality of area values, a plurality of derivatives, etc.

In some embodiments, the data relating to the heart activities of the first subject may include second data relating to the signal based on the plurality of time values, the plurality of amplitude values, the plurality of area values, and/or the plurality of derivatives relating to the one or more characteristic points. For example, the second data may be a variance, a standard deviation, an interquartile range, an average value, a median value, and/or a weighted value of the plurality of time values. As another example, the second data may be a variance, a standard deviation, an interquartile range, an average value, a median value, and/or a weighted value of the plurality of amplitude values. As another example, the second data may be a variance, a standard deviation, an interquartile range, an average value, a median value, and/or a weighted value of the plurality of area values. As yet another example, the second data may be a variance, a standard deviation, an interquartile range, an average value, a median value, and/or a weighted value of the plurality of derivatives.

In some embodiments, the data relating to the heart activities of the first subject may include third data relating to the signal by transforming the signal from the time domain to the frequency domain. The time-frequency transformation may include but is not limited to the Fourier transform, the wavelet transform, the Laplace transform, the Z-transform, or the like, or any combination thereof. The Fourier transform may include, but is not limited to, Prime-factor FFT algorithm, Bruun's FFT algorithm, Rader's FFT algorithm, Bluestein's FFT algorithm, etc.

In some embodiments, the data obtaining module 402 may use the Fourier transform to transform the signal from the time domain to the frequency domain and then determine a first representation in the frequency domain. The data obtaining module 402 may determine the third data based on the first representation. For example, the first representation may be expressed by Equation (1):

$$f(x) = \frac{a_0}{2} + \sum_{l=1}^{\infty} [a_l \cdot \cos(l \cdot x) + b_l \cdot \sin(l \cdot x)], \quad (1)$$

where $a_l$ ($l=0, 1, 2, \ldots, \infty$) and $b_l$ ($l=1, 2, \ldots, \infty$) may refer to coefficients associated with $\cos(l \cdot x)$ and $\sin(l \cdot x)$, respectively. The processor 400 may determine the third data based one the coefficients of Equation (1). For example, the third data may include $a_l$ ($l=0, 1, 2, \ldots, \infty$) and/or $b_l$ ($l=1, 2, \ldots, \infty$).

In some embodiments, the data obtaining module 402 may use the wavelet transform to transform a portion of the signal from the time domain to the frequency domain and then determine a second representation in the frequency domain. The portion of the signal may include at least one beat of the signal. The data obtaining module 402 may determine the third data based on the second representation. For example, the second representation may be expressed by Equation (2):

$$X(g, h) = \frac{1}{h} \cdot \int_{-\infty}^{\infty} x(t) \cdot \Psi\left(\frac{t-g}{h}\right) \cdot dt, \quad (2)$$

where $X(g, h)$ may refer to the portion of the signal in the frequency domain, h may refer to the scale factor, g may refer to the central position of the portion of the signal. The processor 400 may determine the third data based on the coefficients of Equation (2). For example, the third data may be associated with m and/or n.

It should be noted that Equation (1) and Equation (2) are for illustrative and the present disclosure is not intended to be limiting. The representation in frequency domain may have other forms. Accordingly, the third data may be in other forms.

In some embodiments, the data relating to the heart activities of the first subject may be stored in the measuring device 110, the terminal 140, and/or the storage device 160.

In some embodiments, the data relating to the first subject may include personal information relating to the first subject. The personal information relating to the first subject may include registration information/log in information such as user name and password of the first subject associated with the medical system 100. The personal information relating to the first subject may further include the gender of the first subject, age of the subject, height of the first subject, weight of the first subject, posture of the first subject at a time when the signal is obtained, the time when the signal is obtained, whether or not the first subject is with high blood pressure, whether or not the first subject is under at least one medication, information relating to the at least one medication, names and birthdays of family members, home addresses and phone numbers of the family members, emergency contact information, list of current medications and doses, list of allergies, list of any medical devices (e.g., pacemakers), contact information of the primary doctors, insurance card copies, DNR (do not resuscitate) orders and form, Power of Attorney (POA) forms, or the like, or a combination thereof. The posture of the first subject at the time when the signal is obtained may include lying, sitting, standing, etc. The information relating to the medication may include the medicine that the first subject takes, the dosage of the medicine that the first subject takes, whether or not the dosage of the medicine have changed, changes in detailed records if the dosage of the medicine has changed, the time when the first subject takes the medicine, the length of time the first subject has taken the medicine, and so on. The personal information of the first subject may be stored in the server 120, the terminal 140, the external data source 130, the storage device 160 in advance, and/or the combination thereof. The data obtaining module 402 may obtain the personal information from the terminal 140, the external data source 130, and/or the storage device 160 via the network 150. In some embodiments, the data obtaining module 402 may obtain the personal information from the external data source 130. In some embodiments, the personal information of the first subject may be input by the first subject or other subject through the terminal 140 when the blood pressure of the first subject is predicted.

In 506, the processor 400 (e.g., the feature extracting module 404) may extract target features relating to the first subject from the data relating to the first subject. The target features may refer to features relating to the prediction of the blood pressure of the first subject. The target features may be the input of a prediction model used to determine the preliminary blood pressure of the first subject.

In 508, the processor 400 (e.g., the preliminary blood pressure determination module 406) may determine a preliminary blood pressure of the first subject. In some embodiments, the preliminary blood pressure determination module 406 may determine the preliminary blood pressure of the first subject using the prediction model based on the target features relating to the first subject. The target features may be used as inputs of the prediction model. Then the preliminary blood pressure determination module 406 may designate the output of the prediction model as the preliminary blood pressure of the first subject. The preliminary blood pressure may include a systolic blood pressure and a diastolic blood pressure.

In some embodiments, the prediction model may be trained in advance. And, the trained prediction model may be stored in the server 120 (e.g., a cloud server), the terminal 140, and/or the storage device 160. The preliminary blood pressure determination module 406 may obtain the prediction model from the server 120, the terminal 140, and/or the storage device 160 correspondingly. In some embodiments, the prediction model may be determined by performing one or more operations described in connection with FIGS. 7, 9, and/or 11.

In some embodiments, the processor 400 (e.g., the predicted blood pressure determination module 408) may use the preliminary blood pressure as a final result of the predicted blood pressure of the first subject. As the preliminary blood pressure (e.g., one or both of the systolic blood pressure and the diastolic blood pressure) is determined based on information associated with a large group of subjects, it may not be accurate with respect to a particular subject. Therefore, the processor 400 may need to further optimize the preliminary blood pressure to be adaptive to the particular subject. In some embodiments, an optimization model based on the correlation between the systolic blood pressure and the diastolic blood pressure may be used to optimize the preliminary blood pressure.

Then, in 510, the processor 400 (e.g., the predicted blood pressure determination module 408) may determine the predicted blood pressure of the first subject using the optimization model based on the preliminary blood pressure of the first subject to optimize the preliminary blood pressure. In some embodiments, the optimization model may be trained in advance, and the optimization model may be stored in the server 120 (e.g., a cloud server), the terminal 140, the storage device 160, and/or the combination thereof. The predicted blood pressure determination module 408 may obtain the optimization model from the server 120, the terminal 140, and/or the storage device 160 correspondingly. In some embodiments, the optimization model may be determined by performing one or more operations described in connection with FIG. 13.

In 512, the processor 400 (e.g., the communication module 410) may send the predicted blood pressure of the first subject to the terminal 140 in response to the request. The terminal 140 may correspond to the first subject. For example, the first subject may be the user of the terminal 140. The predicted blood pressure may be displayed on the user interface of the terminal 140.

As another example, one or more other optional steps (e.g., a storing step, a preprocessing step) may be added elsewhere in the exemplary process/method.

In some embodiments, all of the steps described in FIG. 5 may be performed by a signal processor of one component of the medical system 100, e.g., the measuring device 110, the server 120, or the terminal 140. In some embodiments, one or more steps described in FIG. 5 may be performed by different processors in one component of the medical system 100, e.g., the measuring device 110, the server 120, or the terminal 140. In some embodiments, one or more steps described in FIG. 5 may be performed by different processors in different components of the medical system 100, e.g., the measuring device 110, the server 120, or the terminal 140. For example, steps 502 to 512 may be performed by a processor in the server 120. As another example, steps 502 to 508 may be performed by a first processor in the server 120, and steps 510 and 512 may be performed by a second processor in the server 120. As another example, steps 502 and 504 may be performed by a first processor in the terminal 140, steps 506 to 512 may be performed by a second processor in the terminal 140. As another example, steps 502 and 504 may be performed by a processor in the measuring device 110, and steps 506 to 512 may be performed by a processor in the server 120. As still another example, steps 502 and 504 may be performed by a processor in the terminal 140, and steps 506 to 512 may be performed by a processor in server 120.

Figure 6A:
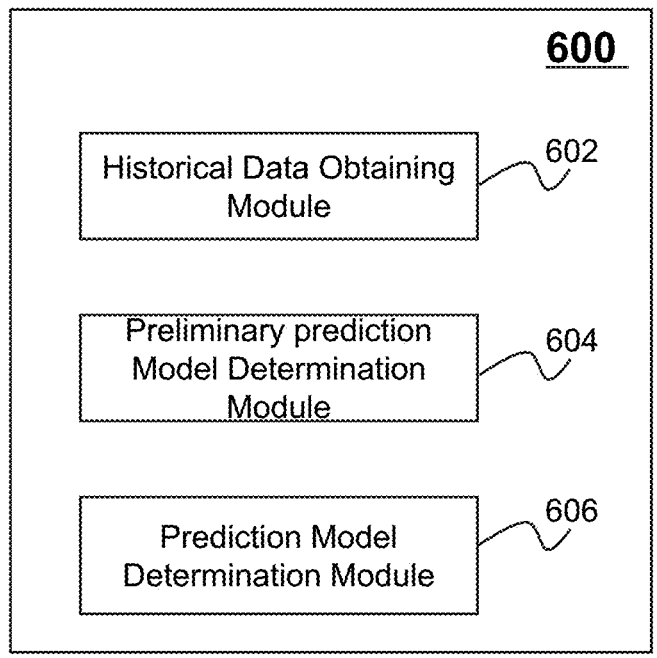
FIGS. 6A and 6B are block diagrams illustrating another exemplary processor according to some embodiments of the present disclosure.
Figure 6B:
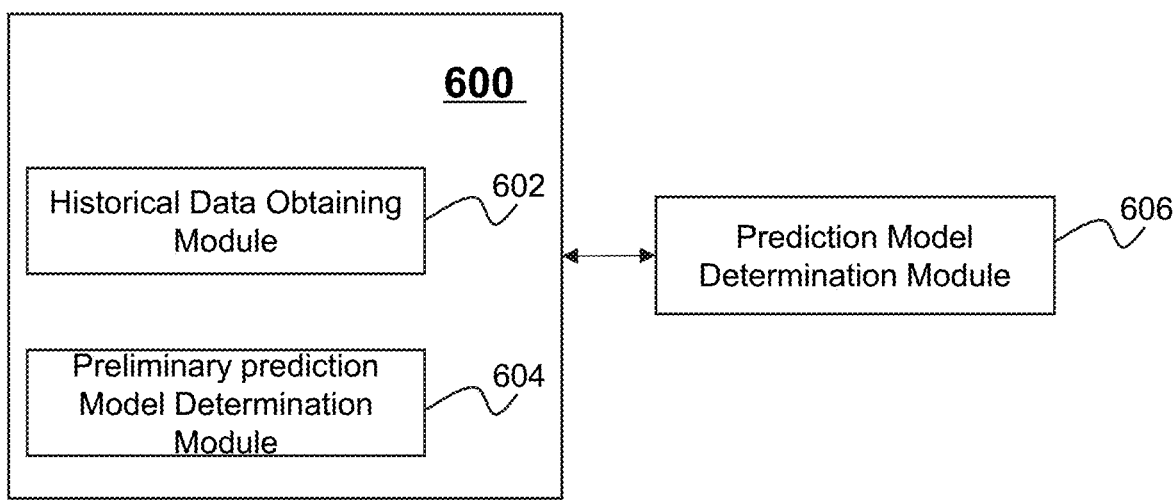

FIGS. 6A and 6B are block diagrams illustrating another exemplary processors according to some embodiments of the present disclosure. As described in FIG. 6A, the processor 600 may include a historical data obtaining module 602, a preliminary prediction model determination module 604, and a prediction model determination module 606. As described in FIG. 6B, the processor 600 may include a historical data obtaining module 602, a preliminary prediction model determination module 604. And another processor may include a prediction model determination module 606. Each module may be a hardware circuit that is designed to perform the following actions, a set of instructions stored in one or more storage media, and/or any combination of the hardware circuit and the one or more storage media. The modules in the processor 600 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. In some embodiments, any two of the modules may be combined as a single module, and any one of the modules may be divided into two or more units.

The historical data obtaining module 602 may obtain historical data relating to a plurality of second subjects and a plurality of historical blood pressure measurements associated with the plurality of second subjects. The historical data relating to the plurality of second subjects may also be referred to herein as a plurality of sets of historical data. Each set of historical data may relate to a historical blood pressure measurement of a second subject. Each of the plurality of historical blood pressure measurements may correspond to one set of the plurality of sets of historical data. As described in connection with 504, the term "historical data" may refer to historical data relating to the heart activities of the plurality of second subjects and the historical personal information relating to the plurality of second subjects. In some embodiments, the term "blood pressure measurements" may refer to historical blood pressure measurements measured by a sphygmomanometer (e.g., an aneroid sphygmomanometer, a mercurial sphygmomanometer, an automatic sphygmomanometer, an electronic sphygmomanometer, etc.).

The preliminary prediction model determination module 604 may generate a preliminary prediction model based on the historical data relating to the plurality of second subjects and the plurality of historical blood pressure measurements associated with the plurality of second subjects obtained by the historical data obtaining module 602. In some embodiments, the preliminary prediction model may include one or more sub preliminary models.

The prediction model determination module 606 may generate a prediction model with respect to the first subject based on the preliminary prediction model and at least part of the historical data relating to the first subject. The at least part of the historical data may correspond to the at least part of features relating to the historical data associated with the preliminary model. In some embodiments, the prediction model determination module 606 may designate a sub prediction model from the one or more sub prediction models of the preliminary prediction model as the prediction model with respect to the first subject based on the at least part of the historical data relating to the first subject.

In some embodiments, all of the modules in FIGS. 6A and 6B may be implemented by in a processor of one component of the medical system 100, e.g., the measuring device 110, the server 120, or the terminal 140. In some embodiments, one or more modules in FIGS. 6A and 6B may be implemented by different processors in one component of the medical system 100, e.g., the measuring device 110, the server 120, or the terminal 140. In some embodiments, one or more modules described in FIGS. 6A and 6B may be included in different processors in different components of the medical system 100, e.g., the measuring device 110, the server 120, or the terminal 140. For example, modules 602 and 604 may be implemented by a processor in the server 120. As another example, modules 602 and 604 may be implemented by a first processor in the server 120, and module 606 may be implemented by a second processor in the server 120. As still another example, modules 602 and 604 may be implemented by a processor in the server 120, and module 606 may be implemented by a processor in the terminal 140.

Figure 7:
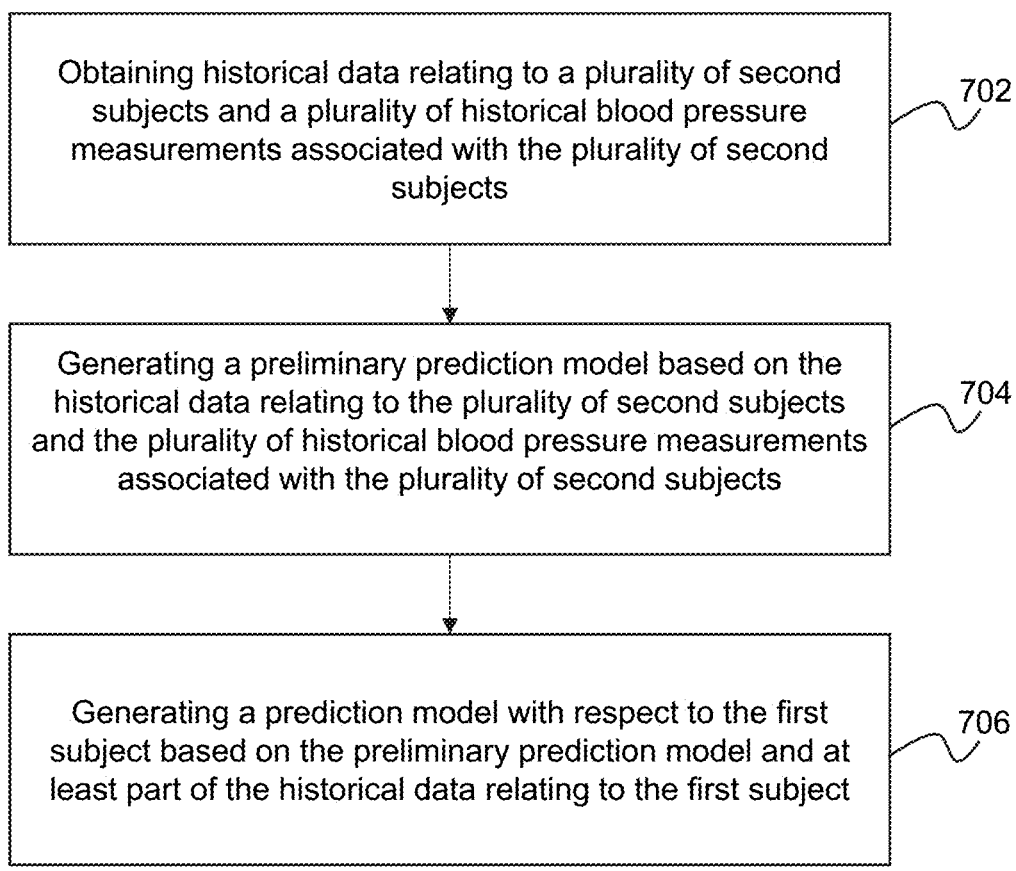
FIG. 7 is a flow chart illustrating a process and/or method for generating a prediction model for predicting a preliminary blood pressure of the first subject according to some embodiments of the present disclosure.

FIG. 7 is a flow chart illustrating a process and/or method for generating a prediction model for predicting a preliminary blood pressure of the first subject according to some embodiments of the present disclosure. The process and/or method 700 may be executed by the medical system 100. For example, the process and/or method 700 may be implemented as a set of instructions (e.g., an application) stored in the storage ROM 230 or RAM 240. The processor 220 (e.g., the processor 600) may execute the set of instructions and may accordingly be directed to perform the process and/or method 700. The operations of the illustrated process/method presented below are intended to be illustrative. In some embodiments, the process/method may be accomplished with one or more additional operations not described, and/or without one or more of the operations discussed. Additionally, the order in which the operations of the process/method as illustrated in FIG. 7 and described below is not intended to be limiting. It should also be noted that the process and/or method 700 may be implemented in the measuring device 110, the server 120, and/or the terminal 140.

In 702, the processor 600 (e.g., the historical data obtaining module 602) may obtain historical data relating to a plurality of second subjects and a plurality of historical blood pressure measurements associated with the plurality of second subjects. The historical data relating to the plurality of second subjects may also be referred to herein as a plurality of sets of historical data. Each set of historical data may relate to a historical blood pressure measurement of a second subject. Each of the plurality of historical blood pressure measurements may correspond to one set of the plurality of sets of historical data. As described in connection with 504, the term "historical data" may refer to historical data relating to the heart activities of the plurality of second subjects and the historical personal information relating to the plurality of second subjects. In some embodiments, the term "blood pressure measurements" may refer to historical blood pressure measurements measured by a sphygmomanometer (e.g., an aneroid sphygmomanometer, a mercurial sphygmomanometer, an automatic sphygmomanometer, an electronic sphygmomanometer, etc.). For each second subject, one or more historical blood pressure measurements may be collected. The historical blood pressure measurements related to each second subject may be collected with respect to one or more postures of each second subject when the blood pressure was measured. The posture may include lying, sitting, standing, etc. In some embodiments, the plurality of historical blood pressure measurements related to each second subject may be collected with respect to the time during a day. For example, the plurality of historical blood pressure measurements may be continuously collected at 9 am every day for three months. In some embodiments, the plurality of historical blood pressure measurements related to each second subject may be collected with respect to the age. For example, the plurality of historical blood pressure measurements may be continuously collected at the annual check-up from 40 to 45 years old. The historical data relating to the plurality of second subjects and the plurality of historical blood pressure measurements associated with the plurality of second subjects may be acquired at any time in the past (e.g., several months ago, several days ago, several hours ago, several minutes ago, etc.). The medical system 100 may save the historical data relating to the plurality of second subjects and the plurality of historical blood pressure measurements associated with the plurality of second subjects as historical data into a storage component in the storage device 160, the external data source 130, or the server 120. In some embodiments, the plurality of second subjects may include the first subject.

The processor 600 (e.g., the historical data obtaining module 602) may determine the historical data relating to the heart activities of the plurality of second subjects based on a plurality of historical signals indicative of the heart activities of the plurality of second subjects. The measuring device 110 may detect physiological phenomenon (e.g., heart activities) and generate the plurality of historical signals at any time in the past (e.g., several months ago, several days ago, several hours ago, several minutes ago, etc.). As described in connection with 504, the historical data relating to the heart activities may include historical first data, historical second data, and historical third data. For each beat of each of the plurality of historical signals, the wave may include one or more characteristic points (e.g., wave crest, trough of the wave, etc.). The historical first data may include a time value, an amplitude value, an area value, a derivative related to each of the one or more characteristic points of each of the plurality of historical signals, etc. The time value and the amplitude value of a characteristic point may be the abscissa and the ordinate of the characteristic point, respectively. The area value may be an integral relating to a time interval. The area value may indicate the change of the blood volume in a vessel close to the attached measuring device 110. The derivative may include a first derivative, a second derivative, a third derivative, a higher derivative, or the like, or a combination thereof. For the plurality of beats, the processor 400 may determine a plurality of time values, a plurality of amplitude values, a plurality of area values, a plurality of derivatives, etc. The historical second data may be a variance, a standard deviation, an interquartile range, an average value, a median value, and/or a weighted value of the plurality of time values, amplitude values, and/or area values, and so on. The historical third data may be associated with coefficients of the plurality of historical signals represented in the frequency domain.

The processor 600 (e.g., the historical data obtaining module 602) may determine the historical personal information relating to the plurality of second subjects. As described in connection with 504, the historical personal information relating to the plurality of second subjects may include the genders of the second subjects, ages of the second subjects, heights of the second subjects, weights of the second subjects, postures of the second subjects when the signals are obtained, the time when the signals are obtained, whether or not the second subjects are with high blood pressure, whether or not the second subjects are under at least one medication, information relating to the at least one medication, names and birthdays of family members, home addresses and phone numbers of the family members, emergency contact information, list of current medications and doses, list of allergies, list of any medical devices (e.g., pacemakers), contact information of the primary care doctor, insurance card copies, DNR (do not resuscitate) orders and form, Power of Attorney (POA) forms, or the like, or a combination thereof. The information relating to the medication of each of the plurality of second subjects may include the medicine that the second subject takes, the dosage of the medicine that the second subject takes, whether or not the dosage of the medicine has changed, changes in detailed records if the dosage of the medicine has changed, the time when the second subject takes the medicine, the length of time the second subject have taken the medicine, or the like, or any combination thereof. In some embodiments, the processor 600 (e.g., the historical data obtaining module 602) may obtain the historical personal information from the server 120 or the storage device 160 via the network 150.

In some embodiments, the processor 600 (e.g., the historical data obtaining module 602) may combine the historical data relating to a plurality of second subjects (also referred to herein as a plurality of historical items) and the plurality of historical blood pressure measurements associated with the plurality of second subjects to generate the sample data for training. The combination of one of the plurality of historical blood pressure measurements and the set of historical data corresponding to the historical blood pressure measurement may be referred to as a historical sample data item. The sample data may correspond to a first predetermined times of measurements for each second subject. The first predetermined times of measurements may include the first one measurement, the first three measurements, the first five measurements, the first ten measurements, etc. In some embodiments, the processor 600 may similarly determine calibration sample data. The calibration sample data may include one historical blood pressure measurement and the set of historical data corresponding to the historical blood pressure measurement. The calibration sample data may correspond to a second predetermined times of measurements for each second subject. The second determined times of measurements may include the second one measurement, the second three measurements, the second five measurements, the second ten measurements, etc. In some embodiments, the sample data may include the calibration sample data. In some embodiments, the sample data and the calibration sample data may or may not overlap. The sample data and the calibration sample data may each include a plurality of sets of data.

In some embodiments, the processor 600 (e.g., the historical data obtaining module 602) may filter the sample data, for example, by determining whether a value of each of the plurality of sample data items is abnormal. When a determination is made that a value of a sample data item is abnormal, the sample data item associated with the abnormal value may be omitted. For example, when the historical blood pressure measurement of the sample data item is identified as a negative value, the processor 600 may omit the sample data item associated with the abnormal historical blood pressure measurement. In some embodiments, the processor 600 may obtain time information relating to each of the plurality of sample data items. The time information relating to each of the plurality of sample data items may refer to the time when the sample data item is acquired by the measuring device 110, e.g., at 8 a.m. in one day, at 2 p.m. in one day. In some embodiments, the processor 600 may divide one day into a predetermined number of groups, e.g., 4 groups, 6 groups. Each group may correspond to a same length of time period. For example, when one day is divided into 6 groups, each of the six groups may have 4 hours. Each group may be associated with a time label. Then the processor 600 may classify the time labels.

In 704, the processor 600 (e.g. the preliminary prediction model determination module 604) may generate a preliminary prediction model based on the historical data relating to the plurality of second subjects and the plurality of historical blood pressure measurements associated with the plurality of second subjects obtained by the historical data obtaining module 602. In some embodiments, the preliminary prediction model may include one or more sub preliminary models.

In some embodiments, the processor 600 may extract the features from the plurality sets of historical data. When training the preliminary prediction model, the processor 600 (e.g. the preliminary prediction model determination module 604) may first normalize the sample data using a normalization technique (e.g., min-max normalization, z-score normalization, decimal scaling normalization). Then, the processor 600 (e.g. the preliminary prediction model determination module 604) may extract features from the normalized sample data. The features may include a plurality of features related to the time values, the amplitude values, the area value of the characteristic points of the historical signals, the second data relating to historical signals, the third data related to the representation in the frequency domain, gender, age, height, weight, posture, measured time, historical blood pressure measurement of each of the plurality of second subjects, whether or not each of the plurality of second subjects is with high blood pressure, whether or not each of the plurality of second subjects is under at least one medication, or the like. The features may also include the time label relating to each of the plurality of sample data items. In some embodiments, the processor 600 (e.g. preliminary prediction model determination module 604) may generate the preliminary prediction model based on the normalized sample data. Detailed description of generating the preliminary prediction model may be in connection with FIG. 9.

In 706, the prediction model determination module 606 may generate a prediction model with respect to the first subject based on the preliminary prediction model and at least part of the historical data relating to the first subject. The at least part of the historical data may correspond to the at least part of features relating to the historical data associated with the first subject. In some embodiments, the processor 600 (e.g. prediction model determination module 606) may designate a sub prediction model from the one or more sub prediction models of the preliminary prediction model as the prediction model with respect to the first subject based on the at least part of the historical data relating to the first subject. Detailed description of generating the preliminary prediction model may be in connection with FIG. 11.

In some embodiments, the prediction model determination module 606 may be implemented by the processor 600, as shown in FIG. 6A. For example, the processor 600 is a processor in the measuring device 110, the server 120, or the terminal 140, and the processor 600 may perform all the operations described in steps 702, 704, and 706 of process/method 700. For instance, the server 120 may obtain the historical data relating to the plurality of second subjects and the plurality of corresponding blood pressure measurements associated with the plurality of second subjects and generate the preliminary prediction model. Because the plurality of second subjects includes the first subject, the server 120 may directly generate the prediction model with respect to the first subject based on the preliminary prediction model and the historical data relating to the first subject. In some embodiments, the prediction model determination module 606 may be implemented by a processor in the measuring device 110 or the terminal 140 instead of the processor 600. For example, the processor 600 is a processor in the server 120, but the prediction model determination module 606 may be implemented by a processor of the measuring device 110 or the terminal 140. Therefore, the operations described in steps 702 and 704 may be performed in the server 120 and the operation described in step 706 may be performed in the measuring device 110 or the terminal 140. For example, the server 120 may first obtain the historical data relating to the plurality of second subjects and the plurality of corresponding blood pressure measurements associated with the plurality of second subjects and generate the preliminary prediction model. Then the server 120 may transmit the preliminary prediction model to the measuring device 110 or the terminal 140, then the measuring device 110 or the terminal 140 may generate the prediction model with respect to the first subject based on the preliminary prediction model and the historical data relating to the first subject. The generated prediction model may be stored in the measuring device 110, the terminal 140, or the combination thereof.

Figure 8:
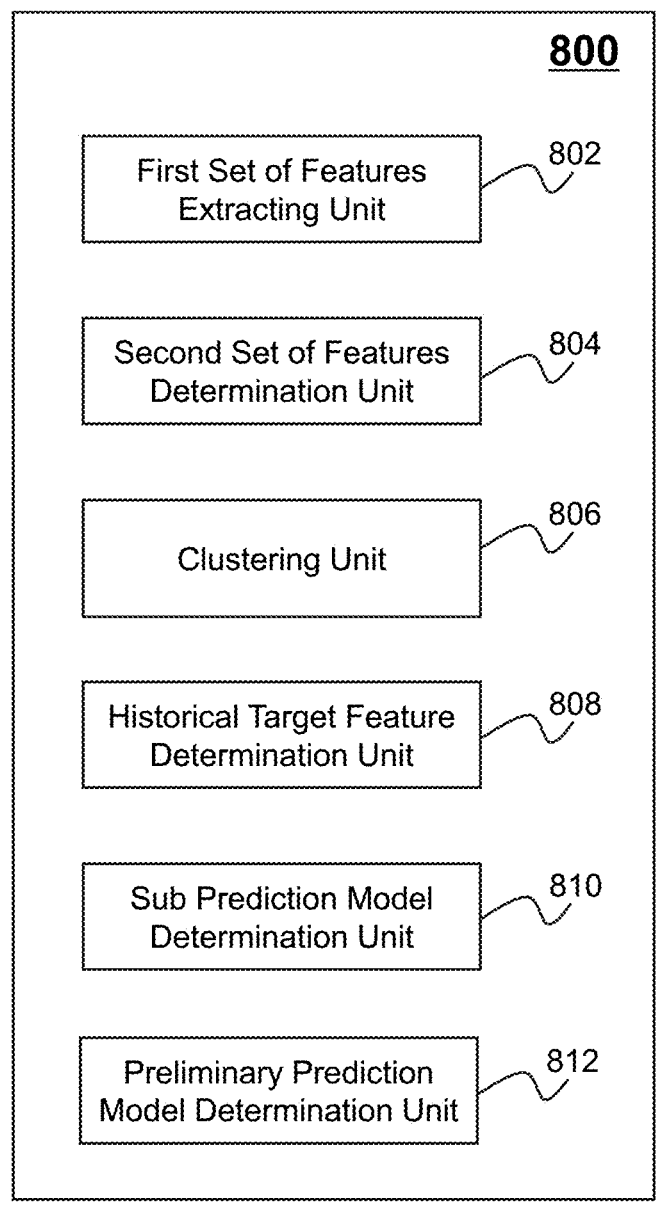
FIG. 8 is a block diagram illustrating an exemplary preliminary prediction model determination module according to some embodiments of the present disclosure.

FIG. 8 is a block diagram illustrating an exemplary preliminary prediction model determination module according to some embodiments of the present disclosure. The preliminary prediction model determination module 800 may include a first set of features extracting unit 802, a second set of features extracting unit 804, a clustering unit 806, a historical target feature determination unit 808, a sub prediction model determination unit 810, and a preliminary prediction model determination unit 812. Each unit may be a hardware circuit that is designed to perform the following actions, a set of instructions stored in one or more storage media, and/or any combination of the hardware circuit and the one or more storage media. The units in the preliminary prediction model determination module 800 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. In some embodiments, any two of the units may be combined as a single unit, and any one of the units may be divided into two or more subunits.

The first set of features extracting unit 802 may extract a first set of features from the plurality of sets of historical data relating to the plurality of second subjects. The first set of features may be related to, for example, the time value, the amplitude value, the area value of the characteristic points of the historical signals, the second data relating to historical signals, the third data related to the representation in the frequency domain, gender, age, height, weight, posture, measured time, historical blood pressure measurement of each of the plurality of second subject, whether or not each of the plurality of second subject is with high blood pressure, whether or not each of the plurality of second subject is under at least one medication, or the like. A dimension of the first set of features may be represented as n1. In some embodiments, the preliminary prediction model determination module 800 may also normalize the first set of features.

The second set of features extracting unit 804 may determine a second set of features based on the normalized first set of features. A dimension of the second set of features may be less than a dimension of the normalized first set of features. The dimension of the second set of features may be represented as n2. n2 is less than n1.

In some embodiments, the second set of features extracting unit 804 may determine the second set of features using a principal component analysis (PCA) based on the normalized first set of features. One of the second set of features may be a linear combination of one or more of the normalized first set of features.

The clustering unit 806 may cluster the plurality of sets of historical data relating to the plurality of second subjects (e.g., the filtered plurality of sets of historical data) into one or more clusters. In some embodiments, the clustering unit 806 may cluster the historical data to the one or more clusters using a clustering algorithm based on the second set of features. The clustering algorithm may include connectivity-based clustering (e.g., single-linkage clustering, complete linkage clustering, average linkage clustering), centroid-based clustering (e.g., k-means clustering, k-medoid clustering), distribution-based clustering (e.g., Gaussian mixture models), density-based clustering (e.g., density-based spatial clustering of applications with noise (DB-SCAN)), or the like, or any combination thereof. The k-medoid clustering may include the partitioning around medoid (PAM) algorithm.

The historical target feature determination unit 808 may determine historical target features based on the second set of features of the training sample data sets. In some embodiments, part of the second set of features may be less related to the prediction of the blood pressure. Therefore, the processor 220 may only select features more related to the prediction of the blood pressure. In some embodiments, the historical target feature determination unit 808 may determine the historical target features from the second set of features using a feature selection technique and information criteria. The feature selection technique may include stepwise regression, penalty method, or the like. The stepwise regression may include but is not limited to forward selection, backward elimination, bidirectional elimination, or the like, or a combination thereof. The penalty method may include Lasso, methods related to the Lasso, Smoothly Clipped Absolute Deviation (SCAD), and methods related to the SCAD, etc. The information criteria may include Bayesian information criterion, Akaike information criterion, deviance information criterion, Hannan-Quinn information criterion, or the like, or a combination thereof. The historical target features may include fixed influence features and random influence features. The fixed influence features may include features with linear correlation with the historical blood pressure measurements, for example, features related to the time value, the amplitude value, the area value of the characteristic points, the medication. The random influence features may include features without linear correlation with the historical blood pressure measurements, but the random influence features may have random influence on the historical blood pressure measurements, for example, a serial number of a feature relating to the characteristic point or the medication.

The sub prediction model determination unit 810 may determine a sub prediction model for each of the one or more clusters based on the historical target features of the historical data in the each cluster and the historical blood pressure measurements corresponding to the historical data in the each cluster. The sub prediction model for each cluster may be a sub prediction model corresponding to a cluster determined by the clustering unit 806. For example, if the clustering unit 806 generates k clusters, the sub prediction model determination unit 810 may generate k sub prediction models.

The preliminary prediction model determination unit 812 may designate the one or more sub prediction models corresponding to the one or more clusters as the preliminary prediction model. The preliminary prediction model may include all of the one or more sub prediction models corresponding to the all of the one or more clusters. The preliminary prediction model may be applicable to different subjects.

Figure 9:
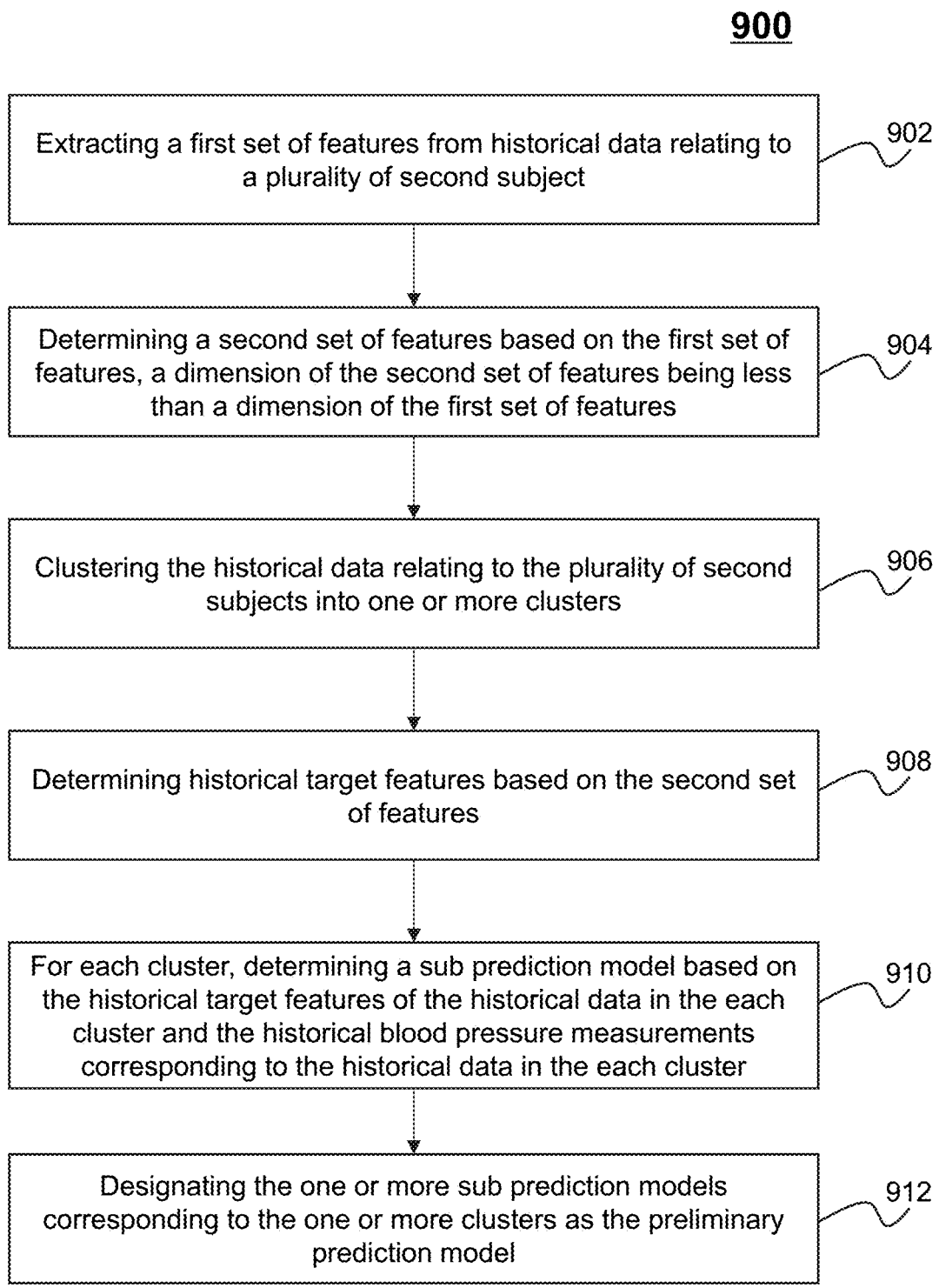
FIG. 9 is a flow chart illustrating a process and/or method for generating a preliminary prediction model according to some embodiments of the present disclosure.

FIG. 9 is a flow chart illustrating a process and/or method for generating a preliminary prediction model according to some embodiments of the present disclosure. The process and/or method 900 may be executed by the medical system 100. For example, the process and/or method 900 may be implemented as a set of instructions (e.g., an application) stored in the storage ROM 230 or RAM 240. The processor 220 may execute the set of instructions and may accordingly be directed to perform the process and/or method 900. The operations of the illustrated process/method presented below are intended to be illustrative. In some embodiments, the process/method may be accomplished with one or more additional operations not described, and/or without one or more of the operations discussed. Additionally, the order in which the operations of the process/method as illustrated in FIG. 9 and described below is not intended to be limiting. It should also be noted that the process and/or method 900 may be implemented in the measuring device 110, the server 120, and/or the terminal 140.

In 902, the processor 220 (e.g. the first set of features extracting unit 802 of the preliminary prediction model determination module 800) may extract a first set of features from the plurality of sets of historical data relating to the plurality of second subjects. The first set of features may be related to, for example, the time value, the amplitude value, the area value of the characteristic points of the historical signals, the second data relating to historical signals, the third data related to the representation in the frequency domain, the time label relating to each of the plurality of sets of historical data, gender, age, height, weight, posture, measured time, the historical blood pressure measurement of each of the plurality of second subject, whether or not each of the plurality of second subject is with high blood pressure, whether or not each of the plurality of second subject is under at least one medication, or the like, or any combination thereof. A dimension of the first set of features may be represented as n1.

In some embodiments, before the processor 220 performs step 902, the processor 220 may first filter the plurality of sets of historical data relating to the plurality of second subjects. For example, the processor 220 may remove the historical data with an abnormal blood pressure value and/or historical data with no blood pressure measurement. Then, the first set of features extracting unit 802 may extract the first set of features from the filtered plurality of sets of historical data.

In some embodiments, before the first set of features extracting unit 802 extracts the first set of features, the processor 220 may normalize the historical data. The normalization of the historical data may include feature scaling and zero mean normalization. The feature scaling may make all of the historical data in a same scale. The zero mean normalization may make the mean value of each of the historical data be zero and the standard deviation of each of the historical data be one.

In 904, the processor 220 (e.g. the second set of features determination unit 804 of the preliminary prediction model determination module 800) may determine a second set of features based on the normalized first set of features. A dimension of the second set of features may be less than a dimension of the normalized first set of features. The dimension of the second set of features may be represented as n2. n2 is less than n1.

In some embodiments, the processor 220 may determine the second set of features using a principal component analysis (PCA) based on the normalized first set of features. One of the second set of features may be a linear combination of one or more of the normalized first set of features. For example, one second feature Z1 may be expressed as Equation (3):

$$Z1 = a1*X1 + a2*X2 + \ldots + ai*Xi, \quad (3)$$

where, $Xi$ may refer to the $i^{th}$ feature of the normalized first set of features, coefficient $ai$ may refer to the coefficient corresponding to the $i^{th}$ feature of the normalized first set of features, and i may refer to an integer large than 0, and less than or equal to n1.

In some embodiments, the dimension of the second set of features n2 may be determined based on a cumulative variance contribution rate set after the principal component analysis of the normalized first set of features. The cumulative variance contribution rate may be a default value in the system or set by an operator of the system. In some embodiments, the cumulative variance contribution rate may be a value from 85% to 95%. In some embodiments, the cumulative variance contribution rate may be a constant value. In some embodiments, the cumulative variance contribution rate may be changed based on a prediction result relating to the whole or part of the historical data. For example, the cumulative variance contribution rate may be set to be as a first number and the prediction is performed on the whole or part of the historical data to generate the prediction result. Then the processor 220 may compare the prediction result with historical blood pressure measurements corresponding to the whole or part of the historical data. When the comparison result does not satisfy a condition, the processor 220 may change the value of the cumulative variance contribution rate until the comparison result satisfies the condition.

In 906, the processor 220 (e.g. the clustering unit 806 of the preliminary prediction model determination module 800) may cluster the plurality of sets of historical data relating to the plurality of second subjects (e.g., the filtered plurality of sets of historical data) into one or more clusters. In some embodiments, the clustering unit 806 may cluster the historical data to the one or more clusters using a clustering algorithm based on the second set of features. The clustering algorithm may include connectivity-based clustering (e.g., single-linkage clustering, complete linkage clustering, average linkage clustering), centroid-based clustering (e.g., k-means clustering, k-medoid clustering), distribution-based clustering (e.g., Gaussian mixture models), density-based clustering (e.g., density-based spatial clustering of applications with noise (DBSCAN)), or the like, or any combination thereof. The k-medoid clustering may include the partitioning around medoid (PAM) algorithm. After clustering, the processor 220 may assign a label to each of the one or more clusters. The processor 220 may further add the label to the second set of features.

In some embodiments, before clustering, the processor 220 (the preliminary prediction model determination module 800) may randomly divide the sample data into training sample data sets and testing sample data sets for a plurality of predetermined times (e.g., 10 times, 50 times, 100 times, 150 times, etc.). Then, for each of the plurality of predetermined times, the preliminary prediction model determination module 800 may only cluster the training sample data sets to generate one or more clusters. The processor 220 may designate one cluster from the one or more clusters to each of the testing sample data sets.

In some embodiments, the training sample data may correspond to part of the plurality of sets of historical data associated with the plurality of the second subjects. The testing sample data sets may correspond to the remaining of the plurality of sets of historical data associated with the plurality of the second subjects. The training sample data sets may correspond to 50%-90% (e.g., 90%, 85%, 80%, 75%, 70%, 65%, 60%, 55%, 50%) of the plurality of sets of historical data. In some embodiments, the training sample data sets and the testing sample data sets may correspond to a first percentage of the plurality of second subjects and a second percentage of the plurality of second subjects, respectively. For example, the training sample data may correspond to 10%, 20%, 30%, or 40% of the plurality of second subjects. The testing sample data sets may correspond to 90%, 80%, 70%, or 60% of the plurality of second subjects correspondingly. The summation of the first percentage and the second percentage may be equal to or less than 1. It should be understood that the above noted values of the first percentage and the second percentage are for illustrative purpose and not intended to be limiting. The first percentage and the second percentage can be any values between 0 and 1. It should be noted that each set of sample data is treated as an entirety during the training and/or testing, and therefore, is indivisible.

In some embodiments, the dividing of the plurality of sets of historical data into the training sample data sets and the testing sample data sets may be processed before the PCA process. For example, the preliminary prediction model determination module 800 may divide the sample data into the training sample data sets and the testing sample data sets before extracting the first set of features from the training sample data. Then the preliminary prediction model determination module 800 may normalize the training sample data and generate one or more normalization parameters. Then the preliminary prediction model determination module 800 may use the one or more normalization parameters to normalize the testing sample data sets. For the normalized training sample data sets and normalized testing sample data sets, the preliminary prediction model determination module 800 may extract the first set of features and perform PCA process.

In 908, the processor 220 (e.g. the historical target feature determination unit 808 of the preliminary prediction model determination module 800) may determine historical target features based on the second set of features of the training sample data. In some embodiments, part of the second set of features may be less related to the prediction of the blood pressure. Therefore, the processor 220 may only select features more related to the prediction of the blood pressure. In some embodiments, the historical target feature determination unit 808 may determine the historical target features from the second set of features using a feature selection technique and information criteria. The feature selection technique may include stepwise regression, penalty method, or the like. The stepwise regression may include but not limited to forward selection, backward elimination, bidirectional elimination, or the like, or a combination thereof. The penalty method may include Lasso, methods related to the Lasso, Smoothly Clipped Absolute Deviation (SCAD), and methods related to the SCAD, etc. The information criteria may include Bayesian information criterion, Akaike information criterion, deviance information criterion, Hannan-Quinn information criterion, or the like, or a combination thereof. The historical target features may include fixed influence features and random influence features. The fixed influence features may include features with linear correlation with the historical blood pressure measurements, for example, features related to the time value, the amplitude value, the area value of the characteristic points, the medication. The random influence features may include features without linear correlation with the historical blood pressure measurements, but the random influence features may have random influence on the historical blood pressure measurements, for example, a serial number of a feature relating to the characteristic point or the medication.

In 910, the processor 220 (e.g. the sub prediction model determination unit 810 of the preliminary prediction model determination module 800) may determine a sub prediction model for each of the one or more clusters based on the historical target features of the historical data in the each cluster and the historical blood pressure measurements corresponding to the historical data in the each cluster. The sub prediction model for each cluster may be a sub prediction model corresponding to a cluster generated in 906. For example, if k clusters are generated in 906, k sub prediction models may be generated in 910. In some embodiments, the sub prediction model may include a generalized linear model.

In some embodiments, the generalized linear model may be expressed by Equation (4):

$$P = q_1 \cdot f(Z1) + q_2 \cdot f(Z2) + \ldots + q_n \cdot f(Zn), \quad (4)$$

wherein, P may refer to a blood pressure, Zi may refer to a historical target features, $1 \leq i \leq n$, n may refer to the total number of the historical target features, f(Zi), may refer to a representation of the historical target feature Zi, and $q_i$ may refer to a coefficient corresponding to the historical target feature Zi. Each of the one or more sub prediction models may be expressed in a similar form as Equation (4).

In 912, the processor 220 (e.g. the preliminary prediction model determination unit 812 of the preliminary prediction model determination module 800) may designate the one or more sub prediction models corresponding to the one or more clusters as the preliminary prediction model. The preliminary prediction model may include all of the one or more sub prediction models corresponding to the all of the one or more clusters. The preliminary prediction model may be applicable to different subjects.

In some embodiments, the processor 220 may test the prediction performance of the trained preliminary prediction model using the testing sample datasets. If the processor 220 determines that the prediction performance of the trained preliminary prediction model meets a predetermined criteria, the processor 220 may use the preliminary prediction model to predict blood pressure. If the processor 220 determines that the preliminary prediction model does not meet the predetermined criteria, the processor 220 (e.g. the preliminary prediction model determination module 800) may update the preliminary prediction model based on the new historical data and blood pressure measurements corresponding to the new historical data.

Figure 10:
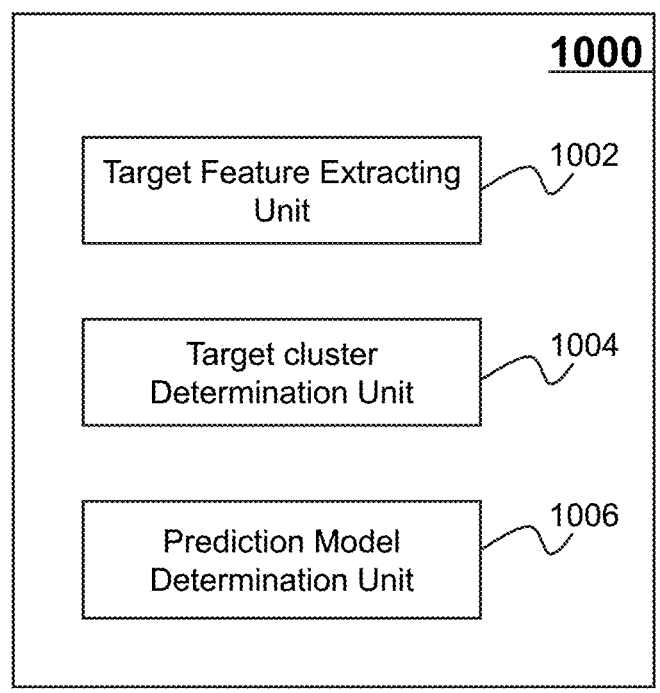
FIG. 10 is a block diagram illustrating an exemplary prediction model determination module according to some embodiments of the present disclosure.

FIG. 10 are block diagrams illustrating an exemplary prediction model determination module according to some embodiments of the present disclosure. The prediction model determination module 1000 may include a target feature extracting unit 1002, a target cluster determination unit 1004, and a prediction model determination unit 1006. Each unit may be a hardware circuit that is designed to perform the following actions, a set of instructions stored in one or more storage media, and/or any combination of the hardware circuit and the one or more storage media. The units in the prediction model determination module 1000 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. In some embodiments, any two of the units may be combined as a single unit, and any one of the units may be divided into two or more subunits.

The target feature extracting unit 1002 may extract historical target features from the historical data relating to the first subject. In some embodiment, the plurality of second subjects may include the first subject and the historical data relating to the plurality of second subjects may include the historical data relating to the first subject. Then the target feature extracting unit 1002 may directly extract the historical target features relating to the first subject from the historical target features determined in 908. In some embodiments, the plurality of second subjects may not include the first subject, the processor 220 may first obtain at least one set of historical data relating to the first subject and a corresponding blood pressure measurement. Then the target feature extracting unit 1002 may extract the target features from the at least one set of historical data relating to the first subject.

The target cluster determination unit 1004 may determine a target cluster from the one or more clusters based on the historical target features of the historical data relating to the first subject. In some embodiments, the target cluster determination unit 1004 may compare the historical target features of the historical data relating to the first subject with the historical target features in the each cluster to determine one of the one or more clusters as the target cluster corresponding to the first subject.

The prediction model determination unit 1006 may designate the sub prediction model corresponding to the target cluster as the prediction model with respect to the first subject.

Figure 11:
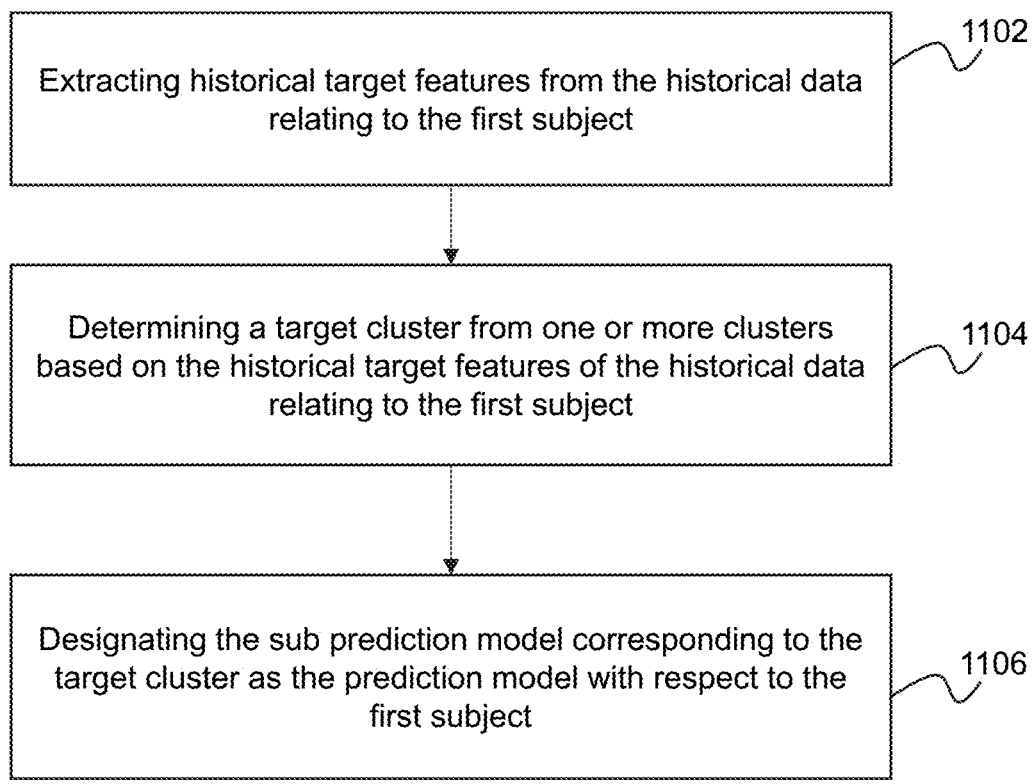
FIG. 11 is a flow chart illustrating a process and/or method for determining a prediction model with respect to the first subject according to some embodiments of the present disclosure.

FIG. 11 is a flow chart illustrating a process and/or method for determining a prediction model with respect to the first subject according to some embodiments of the present disclosure. The process and/or method 1100 may be executed by the medical system 100. For example, the process and/or method 1100 may be implemented as a set of instructions (e.g., an application) stored in the storage ROM 230 or RAM 240. The processor 220 may execute the set of instructions and may accordingly be directed to perform the process and/or method 1100. The operations of the illustrated process/method presented below are intended to be illustrative. In some embodiments, the process/method may be accomplished with one or more additional operations not described, and/or without one or more of the operations discussed. Additionally, the order in which the operations of the process/method as illustrated in FIG. 11 and described below is not intended to be limiting. It should also be noted that the process and/or method 1100 may be implemented in the measuring device 110, the server 120, and/or the terminal 140.

In 1102, the processor 220 (e.g. the target feature extracting unit 1002 of the prediction model determination module 1000) may extract historical target features from the historical data relating to the first subject. In some embodiment, the plurality of second subjects may include the first subject and the historical data relating to the plurality of second subjects may include the historical data relating to the first subject. Then the target feature extracting unit 1002 may directly extract the historical target features relating to the first subject from the historical target features determined in 908. In some embodiments, the plurality of second subjects may not include the first subject, the processor 220 may first obtain at least one set of historical data relating to the first subject and a corresponding blood pressure measurement. Then the target feature extracting unit 1002 may extract the target features from the at least one set of historical data relating to the first subject.

In 1104, the processor 220 (e.g. the target cluster determination unit 1004 of the prediction model determination module 1000) may determine a target cluster from the one or more clusters based on the historical target features of the historical data relating to the first subject. In some embodiments, the processor 220 (e.g. the target cluster determination unit 1004 of the prediction model determination module 1000) may compare the historical target features of the historical data relating to the first subject with the historical target features in the each cluster to determine one of the one or more clusters as the target cluster corresponding to the first subject.

In 1106, the processor 220 (e.g. the prediction model determination unit 1006 of the prediction model determination module 1000) may designate the sub prediction model corresponding to the target cluster as the prediction model with respect to the first subject.

In some embodiments, the prediction model may be updated by the prediction model determination module 1000 based on the updated historical data relating to the first subject and the corresponding blood pressure measurements relating to the first subject. For example, the first subject may suffer from a disease recently and may be under at least one of medication that may have influence on the blood pressure. If the processor 220 still uses the historical data relating to the first subject to determine the prediction model with respect to the first subject, the prediction model may not produce accurate prediction result adaptive to the recent physical condition of the first subject. Therefore, the processor 220 may need to update the prediction model with respect to the first subject using the updated historical data relating to the first subject obtained recently. For example, the processor 220 (e.g. the prediction model determination module 1000) may extract new target features from the updated historical data relating to the first subject, determine an updated target cluster from the one or more clusters based on the updated target features relating to the first subject, and designate the sub prediction model corresponding to the updated target cluster as the updated prediction model with respect to the first subject. The updated prediction model may be more adaptive to the recent physical condition of the first subject. Therefore, the updated prediction model may predict the blood pressure of the first subject more accurately.

Figure 12:
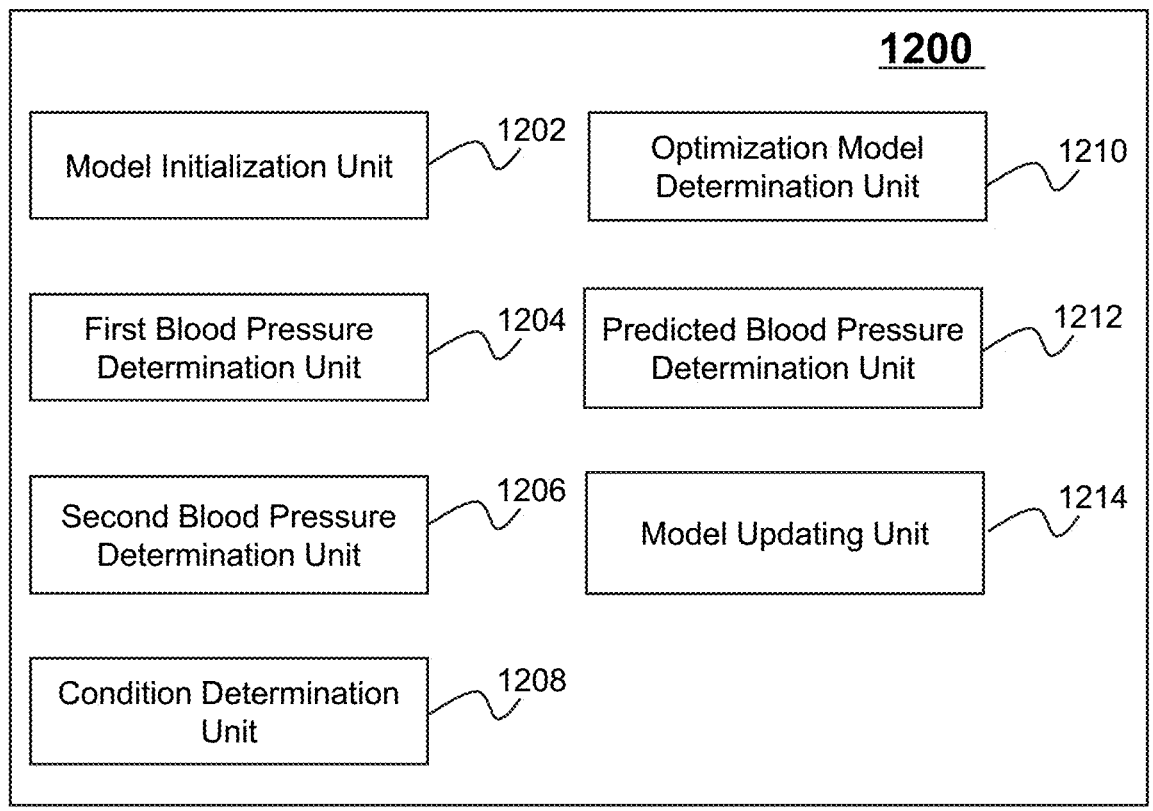
FIG. 12 is a block diagram illustrating an exemplary predicted blood pressure determination module according to some embodiments of the present disclosure.

FIG. 12 is a block diagram illustrating an exemplary predicted blood pressure determination module according to some embodiments of the present disclosure. The predicted blood pressure determination module 1200 may include a model initialization unit 1202, a first blood pressure determination unit 1204, a second blood pressure determination unit 1206, a condition determination unit 1208, an optimization model determination unit 1210, a predicted blood pressure determination unit 1212, and a model updating unit 1214. Each unit may be a hardware circuit that is designed to perform the following actions, a set of instructions stored in one or more storage media, and/or any combination of the hardware circuit and the one or more storage media. The units in the predicted blood pressure determination module 1200 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. In some embodiments, any two of the units may be combined as a single unit, and any one of the units may be divided into two or more subunits.

The model initialization unit 1202 may initialize the optimization model by initializing parameters relating to the optimization model. In some embodiments, the initial values of one or more of the parameters relating to the optimization model may be random values. In some embodiments, the initial values of one or more of the parameters relating to the optimization model may be determined based on the sample data relating to the first subject and the preliminary blood pressure of the first subject determined using the prediction model with respect to the first subject.

The first blood pressure determination unit 1204 may designate the preliminary blood pressure as a first blood pressure. The first blood pressure may include the first systolic blood pressure and the first diastolic blood pressure. The first blood pressure determination unit 1204 may designate the preliminary systolic blood pressure and the preliminary diastolic blood pressure as the first systolic blood pressure and the first diastolic blood pressure, respectively.

In some embodiments, for an iteration, the first blood pressure determination unit 1204 may also designate the blood pressure before the iteration as the first blood pressure.

The second blood pressure determination unit 1206 may generate a second blood pressure based on the first blood pressure using the first optimization model. The second blood pressure may include the second systolic blood pressure and the second diastolic blood pressure.

The condition determination unit 1208 may determine whether or not a converging condition is satisfied. The converging condition may relate to the first blood pressure and the second blood pressure. In some embodiments, the condition determination unit 1208 may determine a standard deviation of the first blood pressure and the second blood pressure and determine whether the standard deviation is smaller than a predetermined threshold. In response to a determination that the standard deviation is smaller than the predetermined threshold, the condition determination unit 1208 may determine that the converging condition is satisfied. In response to a determination that the standard deviation is larger than or the same as the predetermined threshold, the condition determination unit 1208 may determine that the converging condition is not satisfied.

The optimization model determination unit 1210 may determine the optimization model based on the iteration result.

The predicted blood pressure determination unit 1212 may determine the predicted blood pressure of the first subject. For example, the predicted blood pressure determination unit 1212 may designate the second blood pressure generated in an iteration as the predicted blood pressure when the converging condition is satisfied.

The model updating unit 1214 may update the optimization model. For example, the model updating unit 1214 may adjust one or more of the values of the parameters in the optimization model. Then the model updating unit 1214 may generate an updated optimization model.

Figure 13:
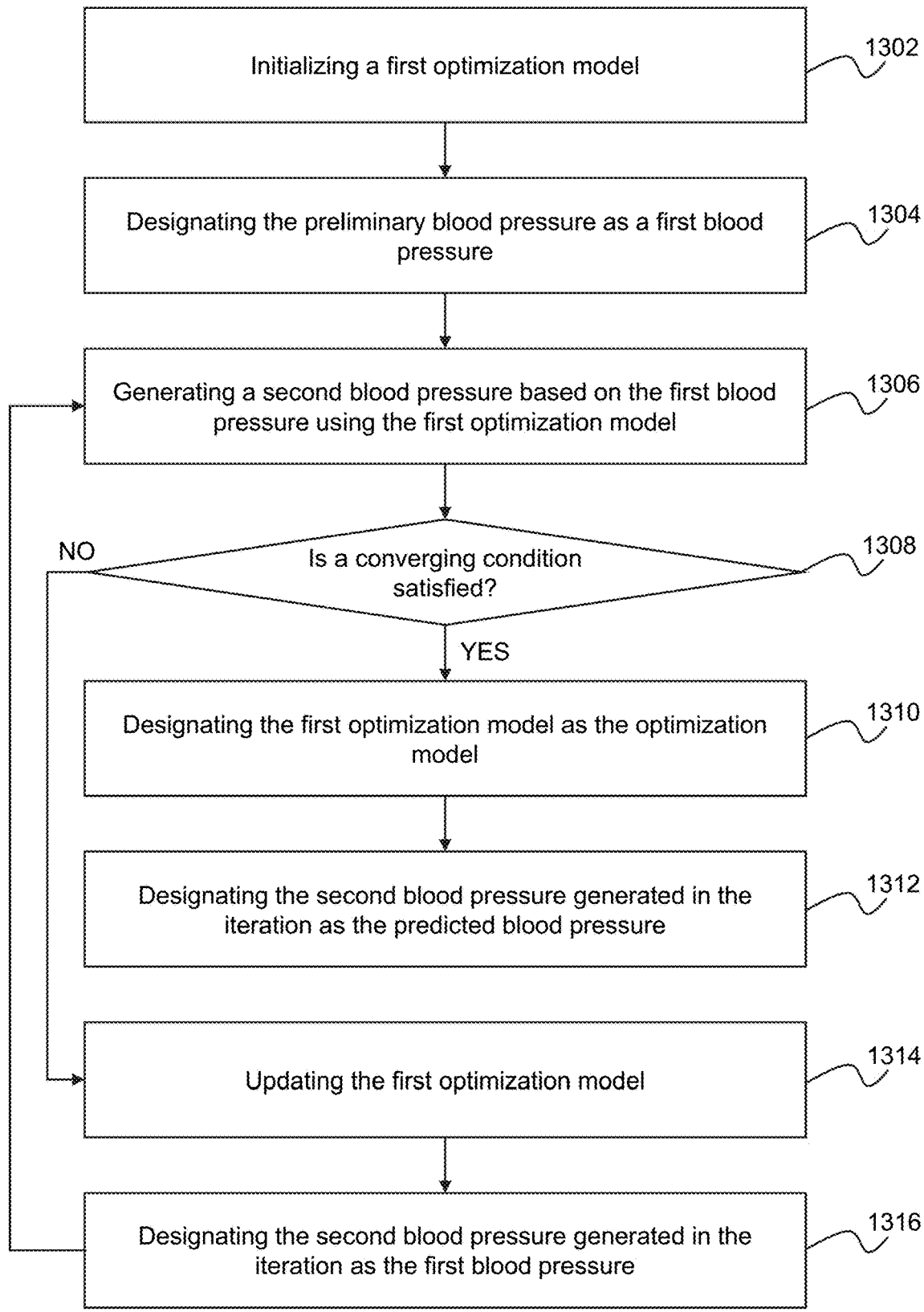
FIG. 13 is a flow chart illustrating a process and/or method for determining a predicted blood pressure of the first subject using an optimization model according to some embodiments of the present disclosure.

FIG. 13 is a flow chart illustrating a process and/or method for determining a predicted blood pressure of the first subject using the optimization model according to some embodiments of the present disclosure. The process and/or method 1300 may be executed by the medical system 100. For example, the process and/or method 1300 may be implemented as a set of instructions (e.g., an application) stored in the storage ROM 230 or RAM 240. The processor 220 may execute the set of instructions and may accordingly be directed to perform the process and/or method 1300. The operations of the illustrated process/method presented below are intended to be illustrative. In some embodiments, the process/method may be accomplished with one or more additional operations not described, and/or without one or more of the operations discussed. Additionally, the order in which the operations of the process/method as illustrated in FIG. 13 and described below is not intended to be limiting. It should also be noted that the process and/or method 1300 may be implemented in the measuring device 110, the server 120, and/or the terminal 140.

As the preliminary blood pressure (e.g., one or both of the systolic blood pressure and the diastolic blood pressure) is determined based on information associated with a large group of subjects, it may not be accurate with respect to a particular subject. Therefore, the processor 220 may need to further optimize the preliminary blood pressure to be adaptive to the particular subject. In some embodiments, an optimization model based on the correlation between the blood pressure and the diastolic blood pressure may be used to optimize the preliminary blood pressure. To determine the predicted blood pressure, the processor 220 may perform one or more iterations to compute the blood pressure until a converging condition is satisfied. The first blood pressure may include a first systolic blood pressure and a first diastolic blood pressure. The second blood pressure may include a second systolic blood pressure and a second diastolic blood pressure.

In 1302, the processor 220 (e.g. the model initialization unit 1202 of the predicted blood pressure determination module 1200) may initialize the optimization model.

In some embodiments, the optimization model may be expressed by Equations (5) and (6):

$$Sbp2=\alpha 1*Dbp1+\beta 1*Y+\delta 1, \quad (5)$$

$$Dbp2=\alpha 2*Dbp1+\beta 2*Y+\delta 2, \quad (6)$$

where Sbp2 may refer to the systolic blood pressure after iteration, Dbp2 may refer to the diastolic blood pressure after iteration, Dbp1 may refer to the diastolic blood pressure before iteration, Y may refer to the target features with respect to the first subject, $\alpha 1$ and $\alpha 2$ may refer to coefficients corresponding to Dbp1, $\beta 1$ and $\beta 2$ may refer to coefficients corresponding to the target features Y, $\delta 1$ and $\delta 2$ may refer to error values. The model initialization unit 1202 may determine initial values for the parameters (e.g., $\alpha 1$, $\alpha 2$, $\beta 1$, $\beta 2$, $\delta 1$, and $\delta 2$) relating to the optimization model. The first optimization model may be initialized when $\alpha 1$, $\alpha 2$, $\beta 1$, $\beta 2$, $\delta 1$, and $\delta 2$ are determined.

In some embodiments, the model initialization unit 1202 of the predicted blood pressure determination module 1200 may initialize $\beta 1$, $\beta 2$, $\delta 1$, and $\delta 2$ based on the sample data relating to the first subject.

In some embodiments, the model initialization unit 1202 of the predicted blood pressure determination module 1200 may initialize $\beta 1$, $\beta 2$, $\delta 1$, and $\delta 2$ based on the sample data relating to the first subject and the preliminary blood pressure of the first subject determined above using Equations (7) and (8):

$$Sbp1=\beta 1*Y+\delta 1, \quad (7)$$

$$Dbp1=\beta 2*Y+\delta 2, \quad (8)$$

wherein, the Sbp1 may refer to the preliminary systolic blood pressure determined using the prediction model, Dbp1 may refer to the preliminary diastolic blood pressure determined using the prediction model, Y may refer to the target features with respect to the first subject, $\beta 1$ may refer to coefficients of the target features Y corresponding to the preliminary systolic blood pressure, $\beta 2$ may refer to coefficients of the target features Y corresponding to the preliminary diastolic blood pressure, $\delta 1$ may refer to an error value corresponding to the preliminary systolic blood pressure, and $\delta 2$ may refer to an error value corresponding to the preliminary diastolic blood pressure. Based on the target features extracted from the sample data relating to the first subject and the preliminary blood pressure (including the preliminary systolic blood pressure and the preliminary diastolic blood pressure), the model initialization unit 1202 may determine the values of the parameters including $\beta 1$, $\beta 2$, $\delta 1$, and $\delta 2$. The determined values of the parameters including $\beta 1$, $\beta 2$, $\delta 1$, and $\delta 2$ may be the initial values of the parameters including $\beta 1$, $\beta 2$, $\delta 1$, and $\delta 2$.

In some embodiments, the model initialization unit 1202 may assign random values for $\alpha 1$ and $\alpha 2$.

For illustrative purpose, the initialized optimization model may also be referred to as a first optimization model.

In 1304, the processor 220 (e.g. the first blood pressure determination unit 1204 of the predicted blood pressure determination module 1200) may designate the preliminary blood pressure as a first blood pressure. The first blood pressure may include the first systolic blood pressure and the first diastolic blood pressure. The first blood pressure determination unit 1204 may designate the preliminary systolic blood pressure and the preliminary diastolic blood pressure as the first systolic blood pressure and the first diastolic blood pressure, respectively.

In 1306, the processor 220 (e.g. the second blood pressure determination unit 1206 of the predicted blood pressure determination module 1200) may generate a second blood pressure based on the first blood pressure using the first optimization model as described in Equations (5) and (6). Sbp2 and Dbp2 may refer to the second systolic blood pressure and the second diastolic blood pressure, respectively, and Dbp1 may refer to the first diastolic blood pressure.

In 1308, the processor 220 (e.g. the condition determination unit 1208 of the predicted blood pressure determination module 1200) may determine whether or not a converging condition is satisfied. The converging condition may relate to the first blood pressure and the second blood pressure. In some embodiments, the condition determination unit 1208 may determine a standard deviation of the first blood pressure and the second blood pressure and determine whether the standard deviation is smaller than a predetermined threshold. The predetermined threshold may be from 0.001 to 0.1, e.g., 0.01, 0.02, 0.03, 0.04, 0.05, 0.06, 0.07, 0.08, 0.09. In response to a determination that the standard deviation is smaller than the predetermined threshold, the condition determination unit 1208 may determine that the converging condition is satisfied, then the process 1300 may proceed to 1310. In response to a determination that the standard deviation is larger than or the same as the predetermined threshold, the condition determination unit 1208 may determine that the converging condition is not satisfied, then the process 1300 may proceed to 1314.

In some embodiments, the converging condition may include a standard deviation of Sbp1 and Sbp2 (also referred to as systolic standard deviation), and/or a standard deviation of Dbp1 and Dbp2 (also referred to as diastolic standard deviation). In some embodiments, the condition determination unit 1208 may only use one of the systolic standard deviation and the diastolic standard deviation to compare with the predetermined threshold to determine whether the converging condition is satisfied. For example, if the systolic standard deviation or the diastolic standard deviation is smaller than the predetermined threshold, the condition determination unit 1208 may determine that the converging condition is satisfied.

In some embodiments, the condition determination unit 1208 may use both of the systolic standard deviation and the diastolic standard deviation to compare with the predetermined threshold to determine whether the converging condition is satisfied. For example, only when both of the systolic standard deviation and the diastolic standard deviation are smaller than the predetermined threshold, the condition determination unit 1208 may determine that the converging condition is satisfied.

In some embodiments, the condition determination unit 1208 may compare the systolic standard deviation with a first predetermined threshold and compare the diastolic standard deviation with a second predetermined threshold to determine whether the converging condition is satisfied. When the systolic standard deviation is smaller than the first predetermined threshold and the diastolic standard deviation is smaller than the second predetermined threshold, the condition determination unit 1208 may determine that the converging condition is satisfied. The first predetermined threshold may be different from the second predetermined threshold. The first predetermined threshold and/or the second predetermined threshold may be from 0.001 to 0.1, e.g., 0.01, 0.02, 0.03, 0.04, 0.05, 0.06, 0.07, 0.08, 0.09.

In 1310, the processor 220 (e.g. the optimization model determination unit 1210 of the predicted blood pressure determination module 1200) may designate the first optimization model as the optimization model. The processor 220 may use the optimization model to generate a predicted blood pressure with respect to the first subject.

In 1312, the processor 220 (e.g. the predicted blood pressure determination unit 1212 of the predicted blood pressure determination module 1200) may designate the second blood pressure generated in the iteration as the predicted blood pressure. The predicted blood pressure may be displayed on a user interface of the terminal 140 associated with the first subject.

In 1314, the processor 220 (e.g. the model updating unit 1214 of the predicted blood pressure determination module 1200) may update the first optimization model. For example, the model updating unit 1214 may adjust one or more of the values of $\alpha 1$, $\alpha 2$, $\beta 1$, $\beta 2$, $\delta 1$, and $\delta 2$ in the first optimization model. Then, the processor 220 (e.g. the model updating unit 1214 of the predicted blood pressure determination module 1200) may generate an updated first optimization model.

In 1316, the processor 220 (e.g. the first blood pressure determination unit 1204 of the predicted blood pressure determination module 1200) may designate the second blood pressure generated in the iteration as the first blood pressure. Then, the process 1300 may return back to 1306 to generate a new second blood pressure based the first blood pressure and the updated first optimization model.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment," "one embodiment," or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 1703, Perl, COBOL 1702, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a software as a service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for determining a blood pressure, comprising:
   at least one storage medium including a set of instructions;
   a communication platform connected to a network; and
   at least one processor in communication with the at least one storage medium, wherein when executing the set of instructions, the at least one processor is directed to:
   receive a request to determine a blood pressure of a first subject from a terminal;
   obtain data relating to the first subject, the data relating to the first subject including data relating to heart activity of the first subject and personal information relating to the first subject, wherein the personal information relating to the first subject includes posture of the first subject at a time when a signal is obtained;
   extract target features relating to the first subject from the data relating to the first subject;
   determine a preliminary blood pressure of the first subject using a prediction model based on the target features relating to the first subject, wherein the prediction model is generated via a first training process, the first training process comprising:
   obtaining historical data relating to a plurality of second subjects and a plurality of historical blood pressure measurements associated with the plurality of second subjects, wherein the plurality of second subjects include the first subject, the historical data relating to the plurality of second subjects includes data relating to heart activities of the plurality of second subjects and historical personal information relating to the plurality of second subjects, and the plurality of historical blood pressure measurements associated with the plurality of second subjects include a plurality of historical blood pressure measurements related to each second subject with respect to one or more postures of the each second subject;
   generating a preliminary prediction model by:
   extracting a first set of features from the historical data relating to the plurality of second subjects;
   determining a second set of features based on the first set of features, a dimension of the second set of features being less than a dimension of the first set of features;
   clustering the historical data relating to the plurality of second subjects into one or more clusters by using a clustering algorithm;
   determining historical target features based on the second set of features;
   for each cluster of the one or more clusters, determining a sub prediction model based on the historical target features of the historical data in the each cluster and the historical blood pressure measurements corresponding to the historical data in the each cluster; and
   designating the one or more sub prediction models corresponding to the one or more clusters as the preliminary prediction model; and
   generating the prediction model with respect to the first subject based on the preliminary prediction model and at least part of historical data relating to the first subject, including:
   extracting historical target features from the historical data relating to the first subject;
   determining a target cluster from the one or more clusters based on the historical target features of the historical data relating to the first subject; and
   designating a sub prediction model corresponding to the target cluster as the prediction model with respect to the first subject; and
   updating the prediction model with respect to the first subject using updated historical data relating to the first subject obtained recently;
   determine a predicted blood pressure of the first subject using an optimization model based on the preliminary blood pressure, wherein to determine the predicted blood pressure of the first subject using the optimization model based on the preliminary blood pressure, the at least one processor is further directed to:
   initialize a first optimization model, including:
   determining initial values of one or more of parameters relating to the first optimization model based on sample data relating to the first subject and the preliminary blood pressure of the first subject by using the prediction model with respect to the first subject;
   designate the preliminary blood pressure as a first blood pressure; and
   iteratively perform operations including:
   generating a second blood pressure based on the first blood pressure using the first optimization model;
   determining whether a converging condition is satisfied based on the first blood pressure and the second blood pressure;
   in response to a determination that the converging condition is satisfied,
   designating the first optimization model as the optimization model and designating the second blood pressure generated in the iteration as the predicted blood pressure; or in response to a determination that the converging condition is not satisfied,
updating the first optimization model and designating the second blood pressure generated in the iteration as the first blood pressure; and
send the predicted blood pressure of the first subject to the terminal in response to the request.

2. The system of claim 1, wherein to obtain the data relating to the heart activity of the first subject, the at least one processor is further directed to:
communicate with a device connected to the first subject, the device being configured to detect the heart activity of the first subject and generate the signal; and
receive from the device, the data relating to the heart activity of the first subject generated based on the signal.

3. The system of claim 1, wherein the generating the preliminary prediction model based on the historical data relating to the plurality of second subjects and the plurality of historical blood pressure measurements associated with the plurality of second subjects further comprises:
normalizing the historical data relating to the plurality of second subjects before extracting the first set of features from the historical data relating to the plurality of second subjects.

4. The system of claim 1, wherein the second set of features are determined using a principal component analysis technique.

5. The system of claim 1, wherein to initialize the first optimization model, the at least one processor is directed to:
obtain a historical blood pressure measurement of the first subject and the historical target features of the first subject; and
initialize the first optimization model based on the historical blood pressure measurement of the first subject and the historical target features of the first subject.

6. The system of claim 1, wherein the predicted blood pressure of the first subject includes a systolic blood pressure and a diastolic blood pressure, and the systolic blood pressure is predicted based on the diastolic blood pressure using the optimization model.

7. The system of claim 1, wherein the data relating to heart activity of the first subject includes:
first data relating to the signal, the first data including at least one of a time value, an amplitude value, an area value, and a derivative related to each of one or more characteristic points;
second data determined by the first data, the second data including at least one of a variance, a standard deviation, an interquartile range, an average value, a median value, and a weighted value of a plurality of time values corresponding to the first data; and
third data relating to the signal by transforming the signal from a time domain to a frequency domain.

8. The system of claim 1, wherein to determine the dimension of the second set of features, the at least one processor is further directed to:
determine the dimension of the second set of features based on a cumulative variance contribution rate set, the cumulative variance contribution rate being changed by comparing a prediction result relating to whole or part of the historical data relating to the plurality of second subjects with historical blood pressure measurements corresponding to the whole or part of the historical data.

9. The system of claim 8, wherein the historical target features determined based on the second set of features include fixed influence features and random influence features, and the random influence features include features without linear correlation with the plurality of historical blood pressure measurements associated with the plurality of second subjects.

10. The system of claim 1, wherein the determining whether the converging condition is satisfied based on the first blood pressure and the second blood pressure includes:
determining a standard deviation of the first blood pressure and the second blood pressure;
determining whether the standard deviation is smaller than a predetermined threshold; and
in response to a determination that the standard deviation is smaller than the predetermined threshold, determining that the converging condition is satisfied, wherein the standard deviation includes a systolic standard deviation and a diastolic standard deviation.

11. The system of claim 10, wherein the determining that the converging condition is satisfied includes:
comparing the systolic standard deviation with a first predetermined threshold;
comparing the diastolic standard deviation with a second predetermined threshold; and
in response to a determination that the systolic standard deviation is smaller than the first predetermined threshold and the diastolic standard deviation is smaller than the second predetermined threshold, determining that the converging condition is satisfied, wherein the first predetermined threshold is different from the second predetermined threshold.

12. The system of claim 1, wherein the updating the prediction model with respect to the first subject using updated historical data relating to the first subject obtained recently includes:
extracting new target features from the updated historical data relating to the first subject;
determining an updated target cluster from the one or more clusters based on the updated target features relating to the first subject; and
designating the sub prediction model corresponding to the updated target cluster as an updated prediction model with respect to the first subject.

13. The system of claim 1, wherein the determining the initial values of the one or more of the parameters relating to the first optimization model based on the sample data relating to the first subject and the preliminary blood pressure of the first subject by using the prediction model with respect to the first subject includes:
determining a coefficient corresponding to the preliminary blood pressure, coefficients corresponding to the target features, and error values based on the preliminary blood pressure of the first subject corresponding to the sample data relating to the first subject and target features extracted from the sample data relating to the first subject; and
designating the coefficient corresponding to the preliminary blood pressure, the coefficients corresponding to the target features, and the error values as the initial values of the one or more of parameters relating to the first optimization model.

14. The system of claim 1, wherein the data relating to heart activities of the plurality of second subjects include historical first data, historical second data, and historical third data, and the historical third data is associated with coefficients of a plurality of historical signals represented in a frequency domain.

15. A method implemented on a computing device having at least one processor, storage, and a communication platform connected to a network for determining a blood pressure, the method comprising:

receiving a request to determine a blood pressure of a first subject from a terminal;

obtaining data relating to the first subject, the data relating to the first subject including data relating to heart activity of the first subject and personal information relating to the first subject, wherein the personal information relating to the first subject includes posture of the first subject at a time when a signal is obtained;

extracting target features relating to the first subject from the data relating to the first subject;

determining a preliminary blood pressure of the first subject using a prediction model based on the target features relating to the first subject, wherein the prediction model is generated via a first training process, the first training process comprising:

obtaining historical data relating to a plurality of second subjects and a plurality of historical blood pressure measurements associated with the plurality of second subjects, wherein the plurality of second subjects include the first subject, the historical data relating to the plurality of second subjects includes data relating to heart activities of the plurality of second subjects and historical personal information relating to the plurality of second subjects; and the plurality of historical blood pressure measurements associated with the plurality of second subjects include a plurality of historical blood pressure measurements related to each second subject with respect to one or more postures of the each second subject;

generating a preliminary prediction model by:

extracting a first set of features from the historical data relating to the plurality of second subjects;

determining a second set of features based on the first set of features, a dimension of the second set of features being less than a dimension of the first set of features;

clustering the historical data relating to the plurality of second subjects into one or more clusters by using a clustering algorithm;

determining historical target features based on the second set of features;

for each cluster of the one or more clusters, determining a sub prediction model based on the historical target features of the historical data in the each cluster and the historical blood pressure measurements corresponding to the historical data in the each cluster; and designating the one or more sub prediction models corresponding to the one or more clusters as the preliminary prediction model; and generating the prediction model with respect to the first subject based on the preliminary prediction model and at least part of historical data relating to the first subject, including:

extracting historical target features from the historical data relating to the first subject;

determining a target cluster from the one or more clusters based on the historical target features of the historical data relating to the first subject; and designating a sub prediction model corresponding to the target cluster as the prediction model with respect to the first subject; and updating the prediction model with respect to the first subject using updated historical data relating to the first subject obtained recently;

determine a predicted blood pressure of the first subject using an optimization model based on the preliminary blood pressure, wherein to determine the predicted blood pressure of the first subject using the optimization model based on the preliminary blood pressure, the method further comprising:

initializing a first optimization model, including:

determining initial values of one or more of parameters relating to the first optimization model based on sample data relating to the first subject and the preliminary blood pressure of the first subject by using the prediction model with respect to the first subject;

designating the preliminary blood pressure as a first blood pressure; and iteratively performing operations including:

generating a second blood pressure based on the first blood pressure using the first optimization model;

determining whether a converging condition is satisfied based on the first blood pressure and the second blood pressure;

in response to a determination that the converging condition is satisfied, designating the first optimization model as the optimization model and designating the second blood pressure generated in the iteration as the predicted blood pressure; or in response to a determination that the converging condition is not satisfied, updating the first optimization model and designating the second blood pressure generated in the iteration as the first blood pressure; and sending the predicted blood pressure of the first subject to the terminal in response to the request.

16. The method of claim 15, wherein the obtaining the data relating to the heart activity of the first subject comprises:

communicating with a device connected to the first subject, the device being configured to detect the heart activity of the first subject and generate the signal; and receiving from the device, the data relating to the heart activity of the first subject generated based on the signal.

17. The method of claim 15, wherein the generating the preliminary prediction model based on the historical data relating to the plurality of second subjects and the plurality of historical blood pressure measurements associated with the plurality of second subjects further comprises:

normalizing the historical data relating to the plurality of second subjects before extracting the first set of features from the historical data relating to the plurality of second subjects.

18. The method of claim 15, wherein the second set of features are determined using a principal component analysis technique.

19. The method of claim 15, wherein the initializing the first optimization model comprises:

obtaining a historical blood pressure measurement of the first subject and the historical target features of the first subject; and initializing the first optimization model based on the historical blood pressure measurement of the first subject and the historical target features of the first subject.

20. A non-transitory computer-readable medium, comprising at least one set of instructions for determining a blood pressure, wherein when executed by at least one processor, the at least one set of instructions directs the at least one processor to:

receive a request to determine a blood pressure of a first subject from a terminal;

obtain data relating to the first subject, the data relating to the first subject including data relating to heart activity of the first subject and personal information relating to the first subject, wherein the personal information relating to the first subject includes posture of the first subject at a time when a signal is obtained;

extract target features relating to the first subject from the data relating to the first subject;

determine a preliminary blood pressure of the first subject using a prediction model based on the target features relating to the first subject, wherein the prediction model is generated via a first training process, the first training process comprising:

obtaining historical data relating to a plurality of second subjects and a plurality of historical blood pressure measurements associated with the plurality of second subjects, wherein the plurality of second subjects include the first subject, the historical data relating to the plurality of second subjects includes data relating to heart activities of the plurality of second subjects and historical personal information relating to the plurality of second subjects; and the plurality of historical blood pressure measurements associated with the plurality of second subjects include a plurality of historical blood pressure measurements related to each second subject with respect to one or more postures of the each second subject;

generating a preliminary prediction model by:

extracting a first set of features from the historical data relating to the plurality of second subjects;

determining a second set of features based on the first set of features, a dimension of the second set of features being less than a dimension of the first set of features;

clustering the historical data relating to the plurality of second subjects into one or more clusters by using a clustering algorithm;

determining historical target features based on the second set of features;

for each cluster of the one or more clusters, determining a sub prediction model based on the historical target features of the historical data in the each cluster and the historical blood pressure measurements corresponding to the historical data in the each cluster; and designating the one or more sub prediction models corresponding to the one or more clusters as the preliminary prediction model; and generating the prediction model with respect to the first subject based on the preliminary prediction model and at least part of historical data relating to the first subject, including:

extracting historical target features from the historical data relating to the first subject;

determining a target cluster from the one or more clusters based on the historical target features of the historical data relating to the first subject; and designating a sub prediction model corresponding to the target cluster as the prediction model with respect to the first subject; and updating the prediction model with respect to the first subject using updated historical data relating to the first subject obtained recently;

determine a predicted blood pressure of the first subject using an optimization model based on the preliminary blood pressure, wherein to determine the predicted blood pressure of the first subject using the optimization model based on the preliminary blood pressure, the at least one processor is further directed to:

initialize a first optimization model, including:

determining initial values of one or more of parameters relating to the first optimization model based on sample data relating to the first subject and the preliminary blood pressure of the first subject by using the prediction model with respect to the first subject;

designate the preliminary blood pressure as a first blood pressure; and iteratively perform operations including:

generating a second blood pressure based on the first blood pressure using the first optimization model;

determining whether a converging condition is satisfied based on the first blood pressure and the second blood pressure;

in response to a determination that the converging condition is satisfied, designating the first optimization model as the optimization model and designating the second blood pressure generated in the iteration as the predicted blood pressure; or in response to a determination that the converging condition is not satisfied, updating the first optimization model and designating the second blood pressure generated in the iteration as the first blood pressure; and send the predicted blood pressure of the first subject to the terminal in response to the request.

\* \* \* \* \*